US008889623B2

(12) United States Patent
Hoeprich et al.

(10) Patent No.: US 8,889,623 B2
(45) Date of Patent: *Nov. 18, 2014

(54) IMMUNOSTIMULATORY NANOPARTICLES AND RELATED COMPOSITIONS, METHODS AND SYSTEMS

(75) Inventors: Paul D. Hoeprich, Pleasanton, CA (US); Nicholas O. Fischer, Livermore, CA (US); Craig Blanchette, Moraga, CA (US); Peter W. Mason, Somerville, MA (US)

(73) Assignees: Lawrence Livermore National Security, LLC, Livermore, CA (US); The Board of Regents of the University of Texas System, Austin, TX (US)

( * ) Notice: Subject to any disclaimer, the term of this patent is extended or adjusted under 35 U.S.C. 154(b) by 813 days.

This patent is subject to a terminal disclaimer.

(21) Appl. No.: 12/604,362

(22) Filed: Oct. 22, 2009

(65) Prior Publication Data
US 2010/0092567 A1 Apr. 15, 2010

Related U.S. Application Data

(63) Continuation-in-part of application No. 12/469,533, filed on May 20, 2009.

(60) Provisional application No. 61/055,380, filed on May 22, 2008.

(51) Int. Cl.
*C07K 14/00* (2006.01)
*A61K 38/00* (2006.01)
*A61K 47/48* (2006.01)

(52) U.S. Cl.
CPC ....... *A61K 47/48853* (2013.01); *A61K 47/4833* (2013.01); *Y10S 977/799* (2013.01)
USPC .............................. 514/12; 530/350; 977/799

(58) Field of Classification Search
None
See application file for complete search history.

(56) References Cited

U.S. PATENT DOCUMENTS

| | | | |
|---|---|---|---|
| 4,317,771 A | 3/1982 | Shiba et al. | |
| 5,393,530 A | 2/1995 | Schneider et al. | |
| 7,048,949 B2 | 5/2006 | Sligar et al. | |
| 7,083,958 B2 | 8/2006 | Sligar et al. | |
| 7,375,234 B2 | 5/2008 | Sharpless et al. | |
| 2005/0182243 A1 | 8/2005 | Sligar et al. | |
| 2006/0189554 A1 | 8/2006 | Mumper et al. | |
| 2006/0211092 A1 | 9/2006 | Sligar et al. | |
| 2007/0117179 A1 | 5/2007 | Kudlicki et al. | |
| 2008/0124350 A1 | 5/2008 | Mumper et al. | |
| 2009/0136937 A1 | 5/2009 | Coleman et al. | |
| 2009/0311276 A1* | 12/2009 | Hoeprich et al. | .......... 424/184.1 |
| 2011/0059549 A1 | 3/2011 | Coleman et al. | |
| 2011/0195450 A1 | 8/2011 | Kudlicki et al. | |

FOREIGN PATENT DOCUMENTS

| | | |
|---|---|---|
| WO | 02/40501 | 5/2002 |
| WO | 2004/094651 | 11/2004 |
| WO | 2005/070400 | 8/2005 |
| WO | 2006/073419 | 7/2006 |
| WO | 2007/053655 | 5/2007 |
| WO | 2008/106660 | 9/2008 |

OTHER PUBLICATIONS

Restriction Requirement issued for U.S. Appl. No. 12/469,533, filed May 20, 2009 in the name of Paul D. Hoeprich et al.; mail date: Jun. 7, 2011.
Non-Final Office Action issued for U.S. Appl. No. 12/469,533, filed May 20, 2009 in the name of Paul D. Hoeprich et al.; mail date: Oct. 24, 2011.
PCT International Search Report for PCT/US2009/044722 filed on May 20, 2009 in the name of Lawrence Livermore National Security, LLC; mail date: Oct. 28, 2010.
PCT Written Opinion for PCT/US2009/044722 filed on May 20, 2009 in the name of Lawrence Livermore National Security, LLC; mail date: Oct. 28, 2010.
Rensen, P.C.N. et al., Recombinant lipoproteins: lipoprotein-like lipid particles for drug targeting, *Advanced Drug Delivery Reviews*, 2001, 47, pp. 251-276.
Bijsterbosch, M.K. et al., Specific Targeting of a Lipophilic Prodrug of Iododeoxyuridine to Parenchymal Liver Cells Using Lactosylated Reconstituted High Density Lipoprotein Particles, *Biochemical Pharmacology*, 1996, vol. 52, pp. 113-121.
Jasanada, F. et al., Indium-111 Labeling of Low Density Lipoproteins with the DTPA-Bis (stearylamide): Evaluation as a Potential Radiopharmaceutical for Tumore Localization, *Bioconjugate Chemistry*, 1996, vol. 7, Issue No. 1, pp. 72-81.
Masquelier, M. et al., Low-Density Lipoprotein as a Carrier of Antitumoral Drugs: In Vivo Fate of Drug-Human Low-Density Lipoprotein Complexes in Mice, *Cancer Research*, Aug. 1986, vol. 46, pp. 3842-3847.
Author Unknown, Special Report, Dengue fever climbs the social ladder, *Nature*, 2007, vol. 448, pp. 734-735.
Gupta, R., et al., Adjuvants for human vaccines—current status, problems and future prospects, Vaccine 1995, 13: 1263-1276.
Okemoto, K., et al., A Potent Adjuvant Monophosphoryl Lipid a Triggers Various Immune Responses, but Not Secretion of IL-1β, or Activation of Caspase-1, The Journal of Immunology 2006, 176: 1203-1208.
Mata-Haro, V., et al., The vaccine adjuvant monophosphoryl lipid A as a TRIF-biased agonist of TLR4, Science 2007, 316: 1628-1632.
Persing, D., et al., Taking toll: lipid A mimetics as adjuvants and immunomodulators, Trends in Microbiology 2002, 10: S32-S37.
Zimmermann, et al., Immunostimulatory DNA as adjuvant: efficacy of phosphodiester CpG oligonucleotides is enhanced by sequence modifications (2003) Vaccine 21:990-995.
Chaung, et al., CpG oligodeoxynucleotides as DNA adjuvants in vertebrates and their applications in immunotherapy (2006) Int'l Immunopharm. 6:1586-1596.
Ruger, et al., In vitro characterization of binding and stability of single-chain Fv Ni-NTA-liposomes, (2006) J. Drug Targeting 14:576-582.

(Continued)

*Primary Examiner* — Anand Desai
(74) *Attorney, Agent, or Firm* — Steinfl & Bruno, LLP

(57) ABSTRACT

Provided herein are immunostimulatory nanolipoprotein particles and related compositions methods and systems.

27 Claims, 15 Drawing Sheets

(56) References Cited

OTHER PUBLICATIONS

Ruger, et al., Generation of immunoliposomes using recombinant single-chain Fv fragments bound to Ni-NTA-liposomes (2005) J. Drug Targeting 13:399-406.
Chikh, et al., Attaching histidine-tagged peptides & proteins to lipid-based carriers through use of metal-ion-chelating lipids (2002) BBA 1567:204-212.
Ulmer, et al.,Vaccine manufacturing: challenges and solutions (2006) Nature Biotech. 24:1377-1383.
Katzen, F., et al., Insertion of Membrane Proteins into Discoidal Membranes using a Cell-free Protein Expression Approach, J. Proteome Res., 2008, vol. 7, pp. 3535-3542.
Cappuccio, et al., Cell-free Co-expression of Functional Membrane Proteins and Apolipoproteins Forming Soluble Nanolipoprotein Particles, (2008) Molecular & Cellular Proteomics 7:2246-2253.
Blanchette, C.D., et al., Characterization and Purification of Polydisperse Reconstituted Lipoproteins and Nanolipoprotein Particles. International Journal of Molecular Sciences 2009, 10:2958-2971.
Blanchette, C.D., et al., Atomic force microscopy differentiates discrete size distributions between membrane protein containing and empty nanolipoprotein particles, Biochimica et Biophysica Acta 1788, 2009, pp. 724-731.
Fischer, N.O., et al., Conjugation to Nickel-Chelating Nanolipoprotein Particles Increases the Potency and Efficacy of Sub-unit Vaccines to Prevent West Nile Encephalitis, Bioconjugate Chem., 2010, vol. 21, pp. 1018-1022.
Petrakova, O., E. Volkova, R. Gorchakov, S. Paessler, R. M. Kinney, and I. Frolov. 2005. Noncytopathic replication of Venezuelan equine encephalitis virus and eastern equine encephalitis virus replicons in Mammalian cells. *J Virol* 79:7597-608.
Konishi, E., and P. W. Mason. 1993. Proper maturation of the Japanese encephalitis virus envelope glycoprotein requires cosynthesis with the premembrane protein. *J Virol* 67:1672-5.
Widman, D. G., T. Ichikawa, R. Fayzulin, N. Bourne, and P. W. Mason. 2008. Construction and characterization of a second-generation pseudoinfectious West Nile virus vaccine propagated using a new cultivation system. *Vaccine* 26:2762-2771.
Hein, C.D., Liu, X-M, and Wang, D. 2008. Click Chemistry, A Powerful Tool for Pharmaceutical Sciences. *Pharmaceutical Research*, vol. 25, No. 10:2216-2230.
Dalpke, A.H., Zimmermann, S., Albrecht, I. & Heeg, K. 2002. Phosphodiester CpG oligonucleotides as adjuvants: polyguanosine runs enhance cellular uptake and improve immunostimulative activity of phosphodiester CpG oligonucleotides in vitro and in vivo. *Immunology* 106:102-112.
Weermata, R.D., McCluskie, M.J., Xu, Y., and Davis, H.L. 2000. CpG DNA induces stronger immune responses with less toxicity than other adjuvants. *Vaccine* 18:1755-62.
Huleatt, J.W., Nakaara, V., Desaia, P., Huanga, Y., Hewitta,D., Jacobs, A., Tanga, J., McDonald, W., Song, L., Evans, R.K., Umlauf, S., Tussey, L., and Powell, T.J. 2007. Potent immunogenicity and efficacy of a universal influenza vaccine candidate comprising a recombinant fusion protein linking influenza M2e to the TLR5 ligand flagellin Vaccine 26:201-214.
Hamdy, S., Haddadi, A., Somayaji, V., Ruan, D. and Samuel, J. 2007. Pharmaceutical analysis of synthetic lipid A-based vaccine adjuvants in poly (d,l-lactic-*co*-glycolic acid) nanoparticle formulations. *Journal of Pharmaceutical and Biomedical Analysis* 44:914-923.
Giannini, S.L., Hanona, E., Moris, P., Van Mechelen, M., Morel, S., Dessy, F., Fourneau, M.A., Colau, B., Suzich, J., Losonksy, G., Martin, M-T., Dubin G., Wettendorff, M.A. 2006. Enhanced humoral and memory B cellular immunity using HPV16/18 L1 VLP vaccine formulated with the MPL/aluminium salt combination (AS04) compared to aluminium salt only. *Vaccine* 24:5937-5949.
Fitzgerald, K.A. and Golenbock, D.T. 2007. The Shape of Things to Come. *Science* 316:1574-1576.
Fischer, N.O., Blanchette, C.D., Chromy, B.A., Kuhn, E.A., Segelke, B.W., Corzett, M., Bench, G., Mason, P.W. and Hoeprich, P.D. 2009.
"Immobilization of His-tagged Proteins on Nickel-Chelating Nanolipoprotein Particles" Bioconjugate Chemistry 20:460-465.
Bayburt, T. H.; Grinkova, Y. V.; Sligar, S. G. 2002, "Self-Assembly of Discoidal Phospholipid Bilayer Nanoparticles with Membrane Scaffold Proteins" *Nano Lett.* 2, 853-856.
Schmitt et al., Synthesis and Characterization of chelator-lipids for reversible immobilization of engineered proteins at self-assembled lipid interfaces, *J. Am. Chem. Soc.* 1994, vol. 116, pp. 8485-8491.
Chromy, B.A., et al., Different Apolipoproteins Impact Nanolipoprotein Particle Formation. *J. Amer. Chem. Soc.* 129, 14348-54 (2007).
Terpe, K., Overview of tag protein fusions: from molecular and biochemical fundamentals to commercial systems. *Appl Microbiol Biotechnol*, 60, 523-33 (2003).
Kolb, H. and Sharpless, B., The growing impact of click chemistry on drug discovery. *Drug Discov. Today*, 8, 1128-37 (2003).
Simon, S.R. and Konigsberg, W.H., Chemical modification of hemoglobins: a study of conformation restraint by internal bridging. *Proc. N.A.S. USA*, 56, 749-56 (1966).
Martin, B.R. and Cravatt, B.F., Large-scale profiling of protein palmitoylation in mammalian cells. *Nat. Methods* 6, 135-38 (2009).
Blanchette, C.D., Quantifying size distributions of nanolipoprotein particles with single-particle analysis and molecular dynamic simulations. *J Lipid Res.* 49, 1420-30 (2008).
Patel, J.D., et al., Preparation and Characterization of Nickel Nanoparticles for Binding to His-tag Proteins and Antigens. *Pharmaceutical Research*, vol. 24, No. 2 (2006).
Lasic et al. "Novel Applications of Liposomes" Trends Biotechnol. 1998, 16, 307-321.
Boroske et al. "Osmotic Shrinkage of Giant Egg-Lecithin Vesicles" Biophys. J. 1981, 34, 95-109.
Disalvo et al. "Surface changes induced by osmotic shrinkage on large unilamellar vesicles" Chem. Phys. Lipids 1996, 84, 35-45.
Choquet et al. "Stability of pressure-extruded liposomes made from archaeobacterial ether lipids" Appl. Microbiol. Biotechnol. 1994, 42, 375-384.
Liang et al. "Mechanical properties and stability measurement of cholesterol-containing liposome on mica by atomic force microscopy" J. Colloid Interface Sci. 2004, 278, 53-62.
Hernández-Caselles et al. "Influence of liposome charge and composition on their interaction with human blood serum proteins" Mol. Cell. Biochem. 1993, 120, 119-126.
Stryer "Lipid Vesicles (Liposomes) and Planar Membranes Are Valuable Model Systems" Biochemistry, 4th Ed. W.H. Freeman and Company, New York: 1995, p. 271.
Kostarelos et al. "Steric stabilization of phospholipid vesicles by block copolymers: Vesicle Flocculation and osmotic swelling caused by monovalent and divalent cations" J. Chem. Soc., Faraday Trans., 1998, 94, 2159-2168.
Ueda, H. et al., Induction of tumor necrosis factor-a in solid tumor region by the orally administered synthetic muramyl dipeptide analogue, romurtide (2001) *Int'l Immunopharm.* 1:97-104.
Osada, Y. et al., Polymorphonuclear Leukocyte Activation by a Synthetic Muramyl Dipeptide Analog (1982) *Inf. Immun.* 38:848-854.
Non-Final Office Action issued for U.S. Appl. No. 12/469,533 in the name of Paul D. Hoeprich; mail date: May 23, 2012.
Ratanabanangkoon, P. et al., Two-Dimensional Streptavidin Crystals on Giant Lipid Bilayer Vesicles, *Langmuir*, 2002, vol. 18, pp. 4270-4276.
Bischler, N. et al., Specific Interaction and Two-Dimensional Crystallization of Histidine Tagged Yeast RNA Polymerase I on Nickel-Chelating Lipids, *Biophysical Journal*, Mar. 1998, vol. 74, pp. 1522-1532.
Kubalek, E.W. et al., Two-Dimensional Crystallization of Histidine-tagged, HIV-1 Reverse Transcriptase Promoted by a Novel Nickel-Chelating Lipid, Journal of Structural Biology, 1994, vol. 113, pp. 117-123.
Final Office Action mailed on Jan. 18, 2012 for U.S. Appl. No. 12/118,396, filed May 9, 2008 in the name of Matthew A. Coleman et l.
Barros, F., et al., Modulation of human erg K+ channel gating by activation of a G protein-coupled receptor and protein kinase C, J. Physiology 1998, 511: 333-346.

(56) References Cited

OTHER PUBLICATIONS

Dong, F., et al., Endothelin-1 enhances oxidative stress, cell proliferation and reduces apoptosis in human umbilical vein endothelial cells: role of ETB receptor, NADPH oxidase and caveolin-1 British J. of Pharmacology 2005, 145: 323-333.
Dumartin, B., et al., Dopamine tone regulates D1 receptor trafficking and delivery in striatel neurons in dopamine transporter-deficient mice, PNAS 2000, 97: 1879-1884.
Gantz, I., et al.,Molecular cloning of a gene encoding the histamine H2 receptor, PNAS 1991, 88: 429-433.
Hauger, R., et al., Corticotropin Releasing Factor (CRF) Receptor Signaling in the Central Nervous System: New Molecular Targets, CNS Neurol. Discord. Drug Target 2006, 5: 453-479.
Hong, Y., et al., G-Protein-Coupled Receptor Microarrays for Multiplexed Compound ScreeningJ. Biomol. Screening 2006, 11: 435-438.
Metz, J., et al ACTH, a-MSH, and control of cortisol release: cloning, sequencing, and functional expression of the melanocortin-2 and melanocortin-5 receptor in *Cyprinus carpio*Am. J. Physiol. Regul. Integr. Comp. Physiol. 2005, 289: R814-R826.
Pettibone, D., et al., The Effects of Deleting the Mouse Neurotensin Receptor NTR1 on Central and Peripheral Responses to NeurotensinJ. Pharma. & Exp. Therapeutics 2002, 300: 305-313.
Ren, X., et al., Different G protein-coupled receptor kinases govern G protein and b-arrestin-mediated signaling of V2 vasopressin receptor, PNAS 2005, 102: 1448-1453.
Adrenergic Receptor, Wikipedia 2006, http://web.archive.org/web/20061230132111/http://en.wikipedia.org/wiki/Adrenergic_Receptor.
5-HT Receptor, Wikipedia 2007, http://web.archive.org/web/20071109235348/http://en.wikipedia.org/wiki/5-HT_receptor.
Muscarinic Acetylcholine Receptor, Wikipedia 2007, http://web.archive.org/web/20071020193657/http://en.wikipedia.org/wiki/Muscarinic_acetylcholine_receptor.
G Protein-coupled Receptor, Wikipedia 2008, http://web.archive.org/web/20080224232212/http://en.wikipedia.org/wiki/G_protein-coupled_receptor.
Advisory Action mailed on Jun. 6, 2012 for U.S. Appl. No. 12/118,530, filed May 9, 2008 in the name of Matthew A. Coleman et al.
Final Office Action mailed on Jun. 7, 2012 for U.S. Appl. No. 12/352,472, filed Jan. 12, 2009 in the name of Sarah E. Baker et al.
Non-Final Office Action issued for U.S. Appl. No. 12/352,548, filed Jan. 12, 2009 in the name of Brett A. Chromy et al., mail date: Sep. 13, 2011.
Notice of Allowance issued for U.S. Appl. No. 12/352,548, filed Jan. 12, 2009 in the name of Brett A. Chromy, mail date: Mar. 12, 2012.
Chefson, A. et al., Progress towards the easier use of P450 enzymes, Mol. bioSyst., 2006, 2, 462-469.
Lubert Stryer et al., Oxygen Binds to a Heme Prosthetic Group, Biochemistry 1995, 4th edition, 148.
Wuu, J. et al., High yield cell-free production of integral membrane proteins without refolding or detergents, BBA 2008, 1778:1237-1250.
Final Office Action for U.S. Appl. No. 12/118,396, filed May 5, 2008 in the name of Matthew A. Coleman et al., mail date: Jan. 18, 2012.
Cullis P.R., et al., Physical Properties and Functional Roles of Lipids in membranes, Biochemistry of Lipids, Lipoproteins and Membranes, 1991, Chapter 1, pp. 1-41.
Silvius, J.R. Thermotropic Phase Transitions of Pure Lipids in Model Membranes and their Modification by Membrane Proteins, Lipid-Protein Interactions, 1982, vol. 2 pp. 239-281.
Non-Final Office Action issued for U.S. Appl. No. 12/118,396, filed May 9, 2008 in the name of Matthew A. Coleman et al.; mail date: Aug. 30, 2011.
Civjan, N.R. et al. Direct solubilization of heterologously expressed membrane proteins by incorporation into nanoscale lipid bilayers, Bio Techniques, 2003, 35(3), pp. 556-559 and 562-563.
Persson, B. et al. Topology prediction of membrane proteins, Protein Science, 1996, vol. 5, pp. 363-371.

Non-Final Office Action mailed on Sep. 22, 2011, U.S. Appl. No. 12/352,472, filed Jan. 12, 2009 in the name of Sarah E. Baker et al.
Restriction Requirement issued for U.S. Appl. No. 12/352,548, filed Jan. 12, 2009 in the name of Brett A. Chromy et al.; mail date: Apr. 25, 2011.
Restriction Requirement issued for U.S. Appl. No. 12/352,472, filed Jan. 12, 2009 in the name of Sarah E. Baker et al.; mail date: May 27, 2011.
Restriction Requirement issued for U.S. Appl. No. 12/118,396, filed May 9, 2008 in the name of Matthew Coleman et al.; mail date: Mar. 4, 2011.
Sapra, R., et al., A simple energy-conserving system: Proton reduction coupled to proton translocation, PNAS 2003, 100: 7545-7550.
Zhang, Y.-H. P.; Evans, B. R.; Mielenz, J. R.; Hopkins, R. C.; Adams, M. W. W. "High-Yield Hydrogen Production from Startch and Water by a Synthetic Enzymatic Pathway", PLoS One 2007, e456, (S), 1-6. May 2007.
Sanderson, K., "The photon trap", Nature 2008, 452, 400-402.
Woodward, J.; Mattingly, S. M.; Danson, M.; Hough, D.; Ward, N.; Adams, M. "In vitro hydrogen production by glucose dehydrogenase and hydrogenase", Nature Biotechnology 1996, 14,872-874.
Woodward, J.; Orr, M.; Cordray, K.; Greenbaum, E., "Enzymatic production of biohydrogen", Nature, 2000, 405, 1014-1015.
Elgren, T. E.; Zadvomy, O. A.; Brecht, E.; Douglas, T.; Zorin, N. A,; Maroney, M. J.; Peters, "Immobilization of Active Hydrogenases by Encapsulation in polymeric porous gels", Nano Letters 2005 vol. 5, No. 10 2085-2087.
Borch, J. et al., "Nanodiscs for immobilization of Lipid Bilayers and Membrane Receptors:," Analytical Chemistry 2008,80, (16), 6245-6252.
Nath, A,; Atkins, W. M.; Sligar, S. G. "Applications of Phospholipid . . . ", Biochemistry 2007,46, (8), 2059-2069.
Boldog, T.; Grimme, S.; Li, M.; Sligar, S.; Hazelbauer, G. L. "Nanodiscs separate chemoreceptor oligomeric states and reveal their signaling properties," Proceedings of the National Academy of Sciences 2006, 103, (31), I 1509-1 1514.
Leitz, A. J.; Bayburt, T. H.; Basnakov, A. N.; Springer, B. A,; Sligar, S. G., "Functional reconstitution of B2-adrenergic receptors utilizing self-assembling Nanodisc technology", Biotechniques 2006, 40, (5), 601-612.
Hedderich, R., "Energy-Converting [NiFi] Hydrogenases From Archaea and Extremophiles", Journal of Bioenergetics and Biomembranes 2004, 36, (1), 65-75.
Vignais PM.; Billoud B. Ocurrence, Classification, and Biological Function of Hydrogenases: An overview. Chemical Reviews 2007, 107, 4206-4272.
Jed O. Eberly and Roger L. Ely, "Thermotolerant Hydrogenases", Critical Reviews in Microbiology, 34:117-130, 2008.
Sun, X. et al . Membrane-Mimetic Films of Aymmetric Phosphtidylcholine Lipid Bolaamphiphiles. Langmuir 2006,22, 1201-1208.
Meyer, J. "Fe/Fe hydrogenases and their evolution: a genomic perspective." Cell. Mol. Life. Sci. 64 2007 1063-1084.
Vincent, K. A. et al. "Investigating and Exploiting the Electrocatalytic Properties of Hydrogenases" Chern. Rev. 2007 107, 4366-4413.
Parkin, A.; Goldet, G. Cavazza, C. Fontecilla-Camps, J., Armstrong, F. J., "The difference a Se Makes?", Am Chern. Soc. 2008,13 (40) 13410-1341 6.
North P. and Fleischer S. "Alteration of Synaptic Membrane Cholesterol/Phospholipid Ratio Using a Lipid Transfer Protein", (1983) J. Biol. Chem. vol. 258, No. 2. pp. 1242-1253.
Bockaert J., Brand C., Journot, L. (1997), Do Recombinant Receptor Assays Provide Affinity and Potency. In Receptor Classification: The integration of operational, structural, and transductional information (D.G. Trist, P.P.A. Humphrey, P. Leff, and N.P. Shankley, Eds.). vol. 812. New York, New York Academy of Sciences, pp. 55-70.
Tufteland M. et al., "Peptide Stabilized Amphotericin B nanodisks", Peptides (2007) 28:741-746.
Jonas, A. "Reconstitution of High-Density Lipoproteins", Methods Enzymol. 1986, 128, 553-582.

(56) References Cited

OTHER PUBLICATIONS

Bayburt, T. H.; Grinkova, Y. V.; Sligar, S. G. "Self-Assembly of Discoidal Phospholipid Bilayer Nanoparticles with membrane scaffold proteins", Nano Lett. 2002, 2, 853-856.
J. Wang, S. Link, C.D. Heyes and M.A. El-Sayed, Comparison of the dynamics of the primary events of bacteriorhodopsin in its trimeric and monomeric states, Biophys. J. 83 (2002), pp. 1557-1566.
G. Bacher, R. Korner, A. Atrih, S.J. Foster, P. Roepstorff and G. Allmaier, Negative and positive ion matrix-assisted laser desorption/ionization time-of-flight mass spectrometry and positive ion nano-electrospray ionization quadrupole ion trap mass spectrometry of peptidoglycan fragments isolated from various *Bacillus* species, J. Mass Spectrom. 36 (2001), pp. 124-139.
Sapra R et al, "Purification and characterization of a Membrane-Bound Hydrogenase from the Hyperthermophilic Archaeon Pyrococcus furiosus", J Bacteriol. 2000 182, (12) 3423-3428.
Sapra R et al,. "A simple energy-conserving system: Proton reduction coupled to proton translocation", J Bacteriol 2003, 100 (13), 7545-7550.
Pasini EM et al., In depth analysis of the membrane and cytosolic proteome of red blood cells, 2006 Blood, 108: 791-801.
G. Bacher et al., "Charge-reduced nano electrospray ionization combined with differential mobility analysis of peptides, proteins, glycoproteins, non covalent protein complexes and viruses", Journal of Mass Spectrometry 2001; 36: 1038-1052.
Goldet, G.; Wait, A. F.; Cracknell, J. A,; Vincent, K. A.; Ludwig, M.; Lenz, Friedrich, B.; Armstrong, F. A. , "Hydrogen Production under Aerobic Conditions by Membrane-Bound Hydrogenases from *Ralstonia* Species", Journal of the American Chemical Society 2008, 130, (33),1, 1106-1113.
Cracknell, J. A.; Vincent, K. A.; Ludwig, M.; Lenz, 0.; Friedrich, B.; Armstrong, F. A., "Enzymatic oxidation of H2 in Atmosphere O2", Journal of the American Chemical Society 2007, 130,424-425.
Kovacs, K. L.; Maroti, G.; Rakhely, G., "A novel approach for biohydrogen production", International Journal of Hydrogen Energy 2006, 31, (1 1), 1460-1468.
Ho, D.; Chu, B.; Lee, H.; Brooks, E. K.; Kuo, K.; Montemagno, C. D., "Fabrication of biomolecule-copolymer hybrid nanovesicles as energy conversion systems", Nanotechnology 2005, 16, (12), 3120-3132.
Vincent, K. A.; Cracknell, J. A,; Lenz, O.; Zebger, I.; Friederich, B.; Armstrong, F., "Electrocatalytic hydrogen oxidation by an enyme at high carbon monoxide or oxygen levels", Proceedings of the National Academy of Sciences 2005,102, (47),16951-16954.
Dunn, R. J. et al., "Structure-functions studies on bacteriorhodopsin" Expression of the bacterio-opsin gene *Escherichia coli,* vol. 262, No. 19, pp. 9246-9254, Jul. 5, 1986.
Sonar, S et al., "Cell-Free Synthesis, Functional Refolding and Spectroscopic Characterization of Bacteriorhodopsin, an Integral Membrane Protein", Biochemistry, vol. 32, pp. 13777-13781, Oct. 25, 1993.
Kalmbach, R., et al., "Functional Cell-free synthesis of a seven helix membrane protein: in situ Insertion of Bacteriorhodopsin in Liposomes", J. Mol. Biol. vol. 371, pp. 639-648, 2007.
Bayburt, T. H., et al., "Assembly of single bacteriorhodopsin trimers in bilayer nandiscs", Archives of Biochemistry and Biophysics, pp. 215-222, 2006.
Bayburt, T. H., et al., "Reconstitution and Imaging of a Membrane Protein in a Nanometer-Size Phospholipid Bilayer" Journal of Structural Biology, pp. 37-44, 1998.
Forstner, M., et al., "Carboxyl-Terminal domain of Human Apolipoprotein E: Expression, Purification, and Crystallization", Protein Expression and Purification, vol. 17, pp. 267-272, 1999.
Morrow, J. A., et al., "Functional Characterization of Apolipoprotein E Isoforms Overexpressed in *Escherichia coli*", Protein Expression and Purification, vol. 16,pp. 224-230, 1990.
Jayaraman, S., et al., "Structural Basis for Thermal Stability of Human Low-Density Lopoprotein", Biochemistry 44, pp. 3965-3971, 2005.
Gursky, O., et al., Compex of Human Apolipoprotein C-1 with Phospholipid: Thermodynamic or Kinetic Stability? Biochemistry 41, pp. 7373-7384, 2002.

Coleman, M., et al., "Asp 46 can substitute for Asp 96 as the Schiff Base Proton Donor in Bacteriorhodopsin", Biochemistry 34, pp. 15599-15606, 1995.
Klammt, C., et al., "High level cell-free expression and specific labeling of integral membrane proteins", Eur. J. Biochem, 271, pp. 568-580, 2004.
Klammt, C., et al., "Cell-free expression as an emerging technique for the large scale production of integral membrane protein" FEBS Journal, 273, pp. 4141-4153, 2006.
Sonar, S., et al., "A redirected proton pathway in the bacteriorhodopsin Mutan Tyr-57→Asp", The Journal of Biological Chemistry, vol. 269, No. 46, pp. 28851-28858, Nov. 18, 1994.
Klammt, C., et al., "Evaluation of detergents for the soluble expression of α-helical and β-barrel-type integral membrane proteins by a preparative scale individual cell-free expression system", FEBS Journal, pp. 6024-6038, 2005.
Camarero, J. A., et l., "Chemoselective Attachment of Biologically Active Protein to Surfaces by Expressed Protein Ligation and Its Application for Protein Chip Fabrication", J.A. Chem. Soc., vol. 126, pp. 14730-14731, 2004.
Rao, R.S., et al., "Comparison of Multiplexed techniques for detection of bacterial and Viral Proteins", Journal of Proteome Research, 3, pp. 736-742, 2004.
Segelke, B. W., et al., "Laboratory scale structural genomics", Journal of Structural and Functional Genomics 5, pp. 147-157, 2004.
Lu, B., et al., "Conformational reorganization of the four-helix bundle of human apolipoprotein E in Binding to Phospholipid", The Journal of Biological Chemistry, vol. 275, No. 27, pp. 20775-20781, Jul. 7, 2000.
Wientzek, M., et al., "Binding of Inspect Apolipophorin III to Dimyristoylphosphatidylcholine Vesicles", The Journal of Biological Chemistry, vol. 269, No. 6, pp. 4605-4612, 1994.
Forte T.M., "Electron microscope study on reassembly of plasma high density apoprotein with various lipids", Biochimi. Biophys. Acta, 248, pp. 381-386, 1971.
Abdulreda, M.H, Atomic Force Microscope Spectroscopy Reveals a Hemifusion Intermediate during Soluble N-Ethylmaleimide Sensitive Factor-Attachment Protein Receptors-Mediated Membrane Fusio, Biophysical Journal,vol. 94, pp. 648-655, Jan. 2008.
Beja, O. et al. Bacterial Phodopsin: Evidence for a New Type of Phototrophy in the Sea, Science, 2000, 2895.5486: 1902-1906.
Shih, A.Y. et al. Molecular Dynamics Simulations of Discoidal Bilayers Assembled from Truncated Human Lipoproteins, Biophysical J., 2005, vol. 88,pp. 548-556.
PCT International Search Report for PCT/US2008/063307 filed on Sep. 5, 2008 in the name of Lawrence Livermore National Security, LLC. Mailed: Oct. 29, 2008.
PCT Written Opinion for PCT/US2008/063307 filed on Sep. 5, 2008 in the name of Lawrence Livermore National Security, LLC. Mailed: Oct. 29, 2008.
Bayburt, T. H., et al., "Self-assembly of single integral membrane proteins into soluble nanoscale phospholipid bilayers", Protein Science vol. 12, No. 11, Nov. 2003, pp. 2476-2481, XP002498218 ISSN: 0961-8368.
Restriction Requirement issued for U.S. Appl. No. 12/118,530, filed May 9, 2008 in the name of Matthew A. Coleman et al.; mail date: Sep. 24, 2010.
Restriction Requirement issued for U.S. Appl. No. 12/118,530, filed May 9, 2008 in the name of Matthew A. Coleman et al.; mail date: Mar. 30, 2011.
Non-Final Office Action issued for U.S. Appl. No. 12/118,530, filed May 9, 2008 in the name of Matthew A. Coleman et al.; mail date: Aug. 30, 2011.
Final Office Action issued for U.S. Appl. No. 12/118,530, filed May 9, 2008 in the name of Matthew A. Coleman et al.; mail date: Jan. 25, 2012.
Advisory Action issued for U.S. Appl. No. 12/118,396, filed May 9, 2008 in the name of Matthew A. Coleman et al.; mail date: Jun. 7, 2012.
Final Office Action issued for U.S. Appl. No. 12/469,533, filed May 20, 2009 in the name of Paul D. Hoeprich et al.; mail date: Dec. 4, 2012.
Non-Final Office Action mailed on Oct. 2, 2013 for U.S. Appl. No. 12/352,472, filed Jan. 12, 2009 in the name of Sarah E. Baker et al.

* cited by examiner

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Gln Thr Leu Ile Ala Ile His Thr Leu Ala Ile Arg Tyr Ala Asn
1               5                   10                  15
```

IMMUNOSTIMULATORY NANOPARTICLES AND RELATED COMPOSITIONS, METHODS AND SYSTEMS

CROSS REFERENCE TO RELATED APPLICATIONS

This application is a continuation in part and claims priority to U.S. patent application entitled "Nanolipoprotein particles and related Compositions Methods and Systems" Ser. No. 12/469,533, filed on May 20, 2009, which on its turn claims priority to U.S. provisional application entitled "Just-In-Time Vaccines Against Select Agent Biothreat Micro-organisms" Ser. No. 61/055,380, filed on May 22, 2008, the disclosure of each of which is incorporated herein by reference in its entirety.

STATEMENT OF GOVERNMENT GRANT

The United States Government has rights in this invention pursuant to Contract No. Contract No. DE-AC52-07NA27344 between the U.S. Department of Energy and Lawrence Livermore National Security, LLC, for the operation of Lawrence Livermore National Security.

TECHNICAL FIELD

The present disclosure relates to immunostimulatory nanoparticles and related compositions, methods and systems. In particular, the present disclosure relates to immunostimulatory nanoparticles suitable to be used in connection with immunogenic compositions such as vaccines.

BACKGROUND

Development of immunogenic compositions, and in particular of vaccines, is currently a challenging effort from conception to actual patient administration.

Some approaches rely on systems for delivering antigens and epitopes and therefore include antigenic epitope discovery (i.e. the molecular portion responsible for eliciting a protective immune response), epitope purification and epitope conjugation.

Other approaches to vaccine development have included and still include passivation of an infectious agent by chemical treatment, e.g. viral formalin fixation or by biological re-engineering to modify known/established virulent genes rendering a non-pathogenic infectious agent.

Additional approaches are based on recombinant proteins, possibly included in immunogenic particles, developed as potential replacements for traditional whole cell or killed pathogen vaccines.

In any of the above approaches, antigens and other immunological agents, such as adjuvants, are typically used to influence the immune system and modulate an immunological response to the antigen of choice [Ref. 13].

SUMMARY

Provided herein, are immunostimulatory nanoparticles formed by a nanolipoprotein particle (NLP) attaching or capable of attaching at least one immunological agent (e.g. an antigen and/or an adjuvant) through binding of the agent with an anchor compound comprised in the NLP. Accordingly, the immunostimulatory nanoparticles herein described allow incorporation of several immunological agents, including antigens and/or adjuvants of various and diverse chemical natures, which can be presented on the NLP, alone or in combination with the other, to provide an immunological construct able to support and/or directly provide an enhanced immune response compared to immunological constructs of the art.

According to a first aspect, an immunostimulatory nanoparticle is described. The immunostimulatory nanoparticle comprises: a scaffold protein, a functionalized membrane-forming lipid presenting an anchor compound substrate, at least one of an antigen and/or an adjuvant attaching an anchor compound, and, optionally, a membrane-forming lipid. In the immunogenic particle at least one of the antigen and/or an adjuvant is attached to the functionalized membrane-forming lipid through binding of the anchor compound substrate with the anchor compound.

According to a second aspect, an immunostimulatory nanoparticle is described. The immunostimulatory nanoparticle comprises a functionalized membrane-forming lipid, a scaffold protein, one or more adjuvants, and optionally a membrane-forming lipid. In the nanolipoprotein particle at least one of the one or more adjuvants attaches an anchor compound, and the functionalized membrane-forming lipid attaches a corresponding anchor substrate compound. In the nanolipoprotein particle, the anchor compound binds the corresponding anchor compound substrate thus attaching each of the one or more adjuvants to the functionalized membrane-forming lipid.

According to a third aspect, an immunostimulatory nanoparticle is described. The immunostimulatory nanoparticle is suitable to attach one or more immunological agents, such as antigens and/or or adjuvants and comprises a functionalized membrane-forming lipid, a scaffold protein, at least one adjuvant, and optionally a membrane-forming lipid. In the nanolipoprotein particle the functionalized membrane-forming lipid presents an anchor compound substrate. In the nanolipoprotein particle, the anchor compound substrate is capable of binding a corresponding anchor compound presented on the immunological agent.

According to a fourth aspect, an immunostimulatory nanoparticle is described. The immunostimulatory nanoparticle is suitable to incorporate one or more adjuvants, and comprises at least one amphipathic adjuvant, a scaffold protein, and optionally a membrane-forming lipid. The amphipathic adjuvant can be either naturally occurring or synthetically derived.

According to fifth aspect, a method to provide an immunological agent in an immunostimulatory nanoparticle is described. The method comprises: attaching the immunological agent to an anchor compound thus providing an anchored immunological agent; attaching the anchored immunological agent to a nanolipoprotein particle comprising a functionalized membrane-forming lipid, a scaffold protein, and optionally a membrane-forming lipid. In the nanolipoprotein particle the functionalized membrane-forming lipid attaches a corresponding anchor compound substrate. In the nanolipoprotein particle, the anchor compound binds the corresponding anchor compound substrate thus attaching the anchored immunological agent to the functionalized membrane-forming lipid of the nanoparticle.

According to a sixth aspect, a system for providing an immunological agent in an immunostimulatory nanoparticle is described. The system comprises: an anchor compound, a functionalized membrane-forming lipid, a scaffold protein, and optionally a membrane-forming lipid, wherein upon binding of the anchor compound with an immunological agent of inters and upon assembly of the functionalized membrane-forming lipid, the scaffold protein and the target protein in a nanolipoprotein particle, the immunological agent of interest is presented on a resulting nanolipoprotein particle.

According to a seventh aspect, an immunostimulatory composition is described, the composition comprising at least one immunostimulatory particle herein described and a suitable vehicle. In some embodiments, the immunostimulatory composition can also comprise an additional adjuvant and/or antigen.

According to an eighth aspect, a method to stimulate the immune system of an individual is described. The method comprises administering to the individual at least one of the immunostimulatory nanoparticles herein described.

According to a ninth aspect, a system to immunize an individual is described. The system comprises: the immunological particle herein described and at least one of an antigen and an adjuvant, the immunogenic particle and the antigen and/or adjuvant to be administered to an individual to immunize the individual.

The immunostimulatory nanoparticle, methods and systems herein described can be used in connection with delivery and presentation of an antigen in an individual to detect and/or enhance the individual immune response to the antigen.

In particular, in several embodiments, the immunostimulatory nanoparticle methods and systems here described allow co-localized presentation of immunostimulatory agents (e.g. multiple adjuvants, multiple agents, multiple agents and adjuvants) which is expected to result in an improved immunostimulation and in particular immunogenic response.

In this connection, in several embodiments, the immunostimulatory nanoparticle, methods and systems herein described allow a rapid and cost effective development of immunogenic compositions against a broad spectrum of antigens, including antigens for which a vaccine has not been developed, yet.

Additionally, in several embodiments, the immunostimulatory nanoparticle, methods and systems herein described provide an immunostimulatory particulate delivery/platform system that combined with recombinant protein epitopes provide a new approach to vaccines development.

Furthermore, in several embodiments, the immunostimulatory nanoparticle, methods and systems herein described allow preparation of an immunogenic composition in an amount of time that is considerably reduced compared with corresponding particles and systems of the art.

More particularly, in several embodiments, the immunogenic nanoparticle, methods and systems herein described allow rapid preparation of relatively stable vaccine compositions capable of eliciting a desired protective immune response against any attached antigen.

Additionally, in several embodiments, the immunostimulatory nanoparticle, methods and systems herein described can be used as particulate delivery systems, similar in size to certain pathogens while also enabling clustered, oriented and concentrated antigen presentation.

Immunostimulatory nanoparticle, methods and systems herein described allow in several embodiments, a rapid protective immune response originating with the innate (humoral) immune system while providing, simultaneous stimulation of the longer acting cellular-mediated immune response.

In several embodiments, the immunostimulatory nanoparticle, methods and systems herein described allow incorporation in the immunogenic particles of secondary additives to enhance immune response in the individual.

In several embodiments, the immunostimulatory nanoparticle, methods and systems herein described allow developing a universal platform for the delivery and presentation of any protein antigen, including toxin, viral, and bacterial proteins, with concomitant adjuvant activity to enhance the host's immune response.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure.

FIG. 7A shows a schematic illustration of production of an NLP platform according to an embodiment herein described; note, specifically the inclusion of functionalized anchor substrate lipid (in this case nickel-chelating lipids); FIG. 7B shows a schematic illustration of production of an anchor-bearing immunogenic protein according to an embodiment herein described (in this case the recombinant expression of proteins to include a poly-histidine peptide for conjugation to chelated nickel); FIG. 7C shows a schematic illustration of production of an immunogenic NLP from the NLP platform and the anchor-bearing immunogenic protein according to an embodiment herein described (in this case the conjugation of a his-tagged protein to an NLP bearing chelated nickel).

FIG. 8 shows an electrophoresis gel demonstrating conjugation of the NiNLP platform with a His-tagged Env protein from West Nile virus (WNV). NiNLPs incubated with His-tagged ENV at room temperature for 45 minutes were analyzed by denaturing SDS-PAGE. Total sample (T) was compared to retentate fraction (R) after size-exclusion partitioning using a 100 kDa MWCO membrane filter, enabling NiNLPs (>400 kDa) to be separated from unconjugated ENV (50 kDa). Addition of EDTA abrogates any interaction between the protein and the NiNLP, demonstrating that conjugation is due to specific interaction of His-tag and chelated nickel.

FIG. 9A shows NiNLPs alone, FIG. 9B shows NiNLPs+His-tagged protein), and FIG. 9C shows NiNLPs+His-tagged protein in the presence of EDTA. Scale bar is 50 nm. A height increase is observed only when the His-tagged protein is incubated with NiNLP in the absence of EDTA. Discoidal morphology of NiNLPs is demonstrated by AFM, whereby the NiNLP diameter is greater than the NiNLP height.

DETAILED DESCRIPTION

Figure 1:
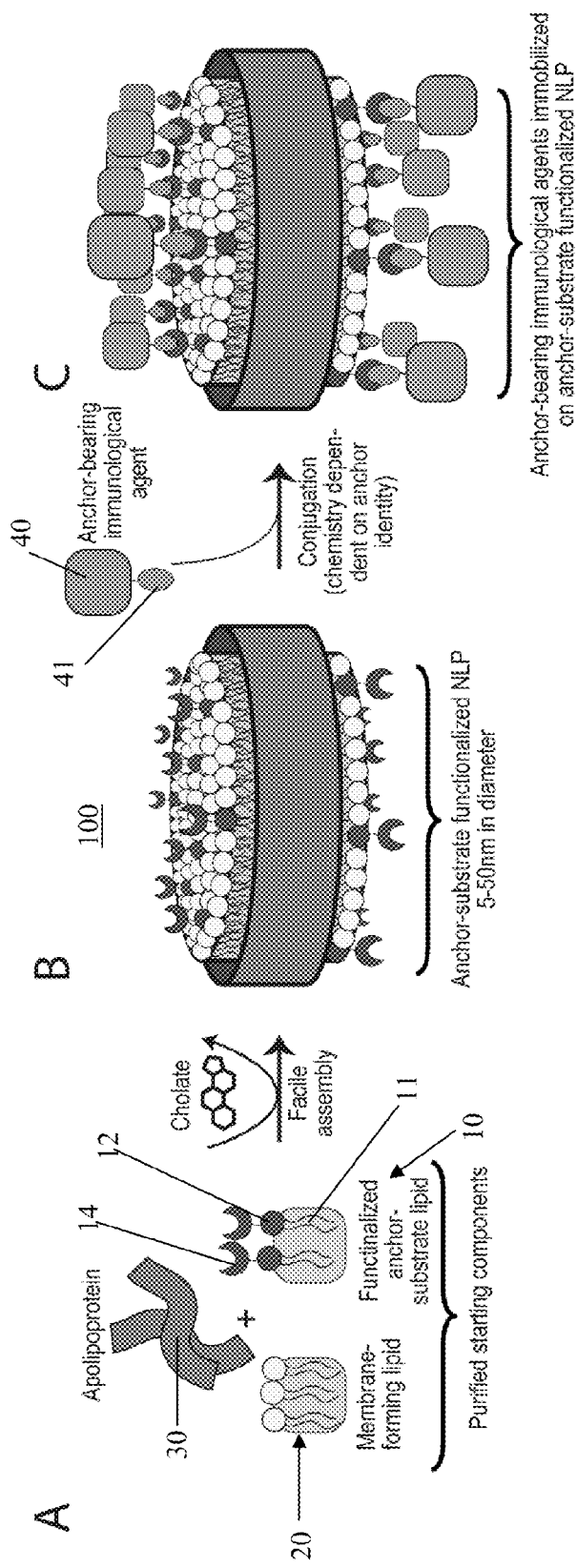
FIG. 1 shows a schematic illustration of assembly of a nanolipoprotein particle comprising a functionalized membrane-forming lipid bearing an anchor compound substrate, according to an embodiment here described. Immunological agents bearing complementary anchor compounds can be immobilized onto the functionalized NLPs.
Figure 2:
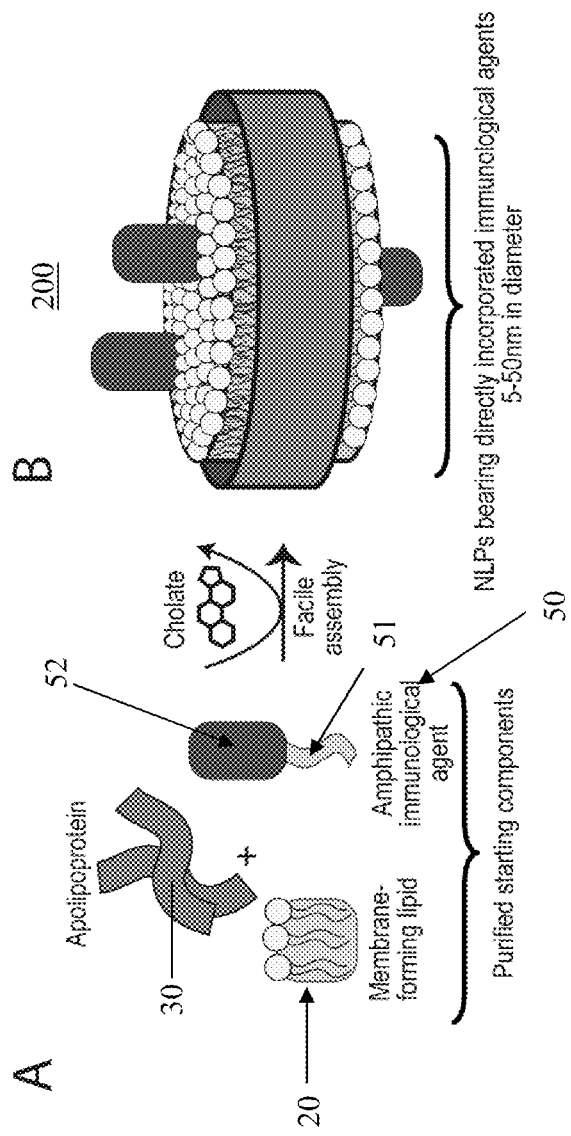
FIG. 2 shows a schematic illustration of assembly of a nanolipoprotein particle comprising an amphipathic adjuvant directly incorporated into the NLP lipid bilayer, according to an embodiment herein described.

An immunostimulatory particle is herein described that is formed by a nanolipoprotein or NLP particle.

The term immunostimulatory as used herein describes the stimulation of the immune system and in particular the ability of a compound, complex and/or particle to affect the immune system. The terms "nanolipoprotein particle", "rHDL", or "NLP" as used herein indicates a supramolecular complex formed by a membrane-forming lipid and a scaffold protein. In particular, nanolipoprotein particles are nano-sized particles comprised of partitioned bilayers of membrane-forming lipid stabilized by peripherally associated scaffold proteins which range in size between about 5 and about 50 nm. In particular, predominantly discoidal in shape, these particles can be used in several embodiments as a bilayer mimetic construct wherein a population of phospholipids is corralled by apolipoproteins ranging in size between 10-25 nanometers. Nanolipoprotein size is detectable using techniques such as nondenaturing gradient gel electrophoresis (NDGGE) and size exclusion chromatography (SEC) and additional techniques identifiable by a skilled person upon reading of the present disclosure.

NLPs are obtainable by allowing solubilized membrane-forming lipids and scaffold protein to self-assemble in an aqueous environment in a molar ratio of membrane-forming lipid to scaffold from about 15:1 up to about 400:1. Solubilization of the membrane-forming lipids can be performed by using a detergent, such as cholate, which is associated with the lipids. Removal of this detergent allows self-assembly of the membrane-forming lipid and the scaffold protein. Alternatively, or in addition, the membrane-forming lipids (in the form of small unilamellar vesicles) and scaffold protein can be subjected to temperature cycles according to procedures known in the art.

Exemplary procedures to perform self-assembly of NLPs are described in art, for example in Reference 15, and in other references identifiable by a skilled person. NLPs prepared using these procedures are discoidal in morphology (i.e. non-spheroidal). The NLP height is correlated to the bilayer thickness of the membrane-forming lipid used. Typically, the bilayer thickness is between about 4 and about 7 nanometers, and is dependent on the identity of the membrane-forming lipid. The diameter of the NLPs can be between about 5 and about 50 nanometers, typically ranging between about 10 and about 25 nanometers. By nature of this morphology, a planar surface is present on both sides of the lipid bilayer. Size, structure and discoidal shape of an NLP can be detected by high resolution imaging and sizing techniques such as atomic force microscopy (AFM), transmission electron microscopy (TEM), ion mobility spectrometry and additional techniques suited to analyze particles in the low nanometer size regime identifiable by a skilled person upon reading of the present disclosure [Ref. 15].

The term "membrane-forming lipid" or "amphipatic lipid" as used herein indicates a lipid possessing both hydrophilic and hydrophobic properties that, in an aqueous environment and in the presence of a scaffold protein, assemble in a lipid bilayer structure that consists of two opposing layers of amphipathic molecules known as polar lipids. Each polar lipid has a hydrophilic moiety, i.e., a polar group such as a derivatized phosphate or a saccharide group, and a hydrophobic moiety, i.e., a long hydrocarbon chain(s). Exemplary polar lipids include phospholipids, sphingolipids, glycolipids, ether lipids, and sterols. Amphipatic lipids include but are not limited to membrane lipids, i.e. amphipatic lipids that are constituents of a biological membrane, such as phospholipids like dimyrisoylphosphatidylcholine (DMPC) or dioleoylphosphoethanolamine (DOPE) or dioleoylphosphatidylcholine (DOPC). In some embodiments, the membrane-forming lipid can be a biological molecule, i.e. a molecule produced by a living organism including unicellular organism, such as bacteria or yeasts, and multicellular such as animals, including mammals and humans, and plants. In some embodiments, the membrane-forming lipids can consist of non-lipid amphipathic molecules, for example diglycerol tetraethers, cholesterol, egosterol, and the like.

The term "scaffold protein" as used herein indicates any protein that is capable of self-assembly with an amphipatic lipid in an aqueous environment, organizing the amphipatic lipid into a bilayer, and include but are not limited to apolipoproteins, apolipophorins, derivatives thereof (such as truncated and tandemly arrayed sequences) and fragments thereof (e.g. peptide fragments and synthetic peptides), such as apolipoprotein E4 22K fragment, apolipophorin III, apolipoprotein A-1 and the like. The term "derivative" as used herein indicates a chemical or biological substance that is related structurally to another substance and derivable, at least theoretically, from another substance through a modification of the another substance. In particular, if a first compound is a derivative of a second compound and the second compound is associated with a chemical and/or biological activity, the first compound differs from the second compound for at least one structural feature, while retaining (at least to a certain extent) the chemical and/or biological activity of the second compound and at least one structural feature (e.g. a sequence, a fragment, a functional group and others) associated thereto. A skilled person will be able to identify, on a case by case basis and upon reading of the present disclosure, structural features of the second compound that have to be maintained in the first compound to retain the second compound chemical and/or biological activity as well as assays that can be used to prove retention of the chemical and/or biological activity.

The term "protein" as used herein indicates a polypeptide with a particular secondary and tertiary structure. The term "polypeptide" as used herein indicates an organic polymer composed of two or more amino acid monomers and/or analogs thereof. Accordingly, the term "polypeptide" includes amino acid polymers of any length including full length proteins and peptides, as well as analogs and fragments thereof. A polypeptide of three or more amino acids can be a protein oligomer or oligopeptide. As used herein the term "amino acid", "amino acid monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

The immunostimulatory NLPs herein described are configured to present an immunological agent such as an antigen or an adjuvant.

The term "present" as used herein with reference to a compound or functional group indicates attachment performed to maintain the chemical reactivity of the compound or functional group as attached. Accordingly, a functional group presented on a molecule is able to perform under the appropriate conditions the one or more chemical reactions that chemically characterize the functional group. A compound presented on a particle is able to perform under the appropriate conditions the one or more chemical reactions that chemically characterize the compound. In embodiments, where the compound is or comprises an immunological agent, the immunological agent presented maintains the complex of reactions that are associated with the immunological activity characterizing the agent at issue. Accordingly, presentation of an immunological agent indicates attachment such that the immunological activity associated to the immunological agent attached is maintained.

The term "immunological agent" as used herein indicates a compound that is able to interfere with the immune system of an individual, and in particular provoke, reduce, enhance or impair a response of the immune system under same or comparable conditions. Exemplary immunological agents comprise antigen and adjuvants.

The term "antigen" or "immunogen" as used herein indicates a substance that prompts the generation of antibodies and/or can cause an immune response. In particular, antigens in the sense of the present disclosure encompass all substances that can be recognized by an adaptive immune system. Exemplary antigens include exogenous antigens and endogenous antigens. Exogenous antigens are antigens that have entered the body from the outside, for example by inhalation, ingestion, or injection. By endocytosis or phagocytosis, these antigens are taken into the antigen-presenting cells (APCs) and processed into fragments. APCs then present the fragments to T helper cells ($CD4^+$) by the use of class II histocompatibility molecules on their surface. Some T cells are specific for the peptide: MHC complex. They become activated and start to secrete cytokines. Cytokines are substances that can activate cytotoxic T lymphocytes (CTL), antibody-secreting B cells, macrophages, and other particles. Endogenous antigens are antigens that have been generated within the cell, as a result of normal cell metabolism, or because of viral or intracellular bacterial infection. The fragments are then presented on the cell surface in the complex with MHC class I molecules. If activated cytotoxic $CD8^+$ T cells recognize them, the T cells begin to secrete various toxins that cause the lysis or apoptosis of the infected cell. In order to keep the cytotoxic cells from killing cells just for presenting self-proteins, self-reactive T cells are deleted from the repertoire as a result of tolerance (also known as negative selection). They include xenogenic (heterologous), autologous and idiotypic or allogenic (homologous) antigens. Antigens are also generated between normal cells.

The term "adjuvant" as used herein indicates an agent that stimulates the immune system but that is not antigenic in itself. Typically adjuvants are used in connection with antigens and/or vaccine composition to increase the response to one or more antigen of choice [Refs. 11 and 12].

Accordingly in several embodiments the immunological agent carried by a NLP is an adjuvant or an antigen.

In particular, in immunostimulatory nanoparticles herein described at least one of an antigen or an adjuvant are attached to functionalized membrane-forming lipid through binding of an anchor compound attached to the antigen or adjuvant and a corresponding anchor compound substrate attached to the functionalized membrane-forming lipid.

The term "attach" or "attached" as used herein, refers to connecting or uniting by a bond, link, force or tie in order to keep two or more components together, which encompasses either direct or indirect attachment such that for example where a first compound is directly bound to a second compound or material, and the embodiments wherein one or more intermediate compounds, and in particular molecules, are disposed between the first compound and the second compound or material.

The terms "functionalize" and "functionalization" as used herein, indicates the appropriate chemical modifications of a molecular structure (including a substrate or a compound) resulting in attachment of a functional group to the molecular structure. The term "functional group" as used herein indicates specific groups of atoms within a molecular structure that are responsible for the characteristic chemical reactions of that structure. Exemplary functional groups include, hydrocarbons containing halogen groups, hydrocarbons containing oxygen groups, hydrocarbons containing nitrogen groups, hydrocarbons containing phosphorus groups and hydrocarbons containing sulfur groups, all identifiable by a skilled person.

In several embodiments of the nanolipoprotein particle here described at least a portion or all of the membrane-forming lipid is functionalized with an anchor substrate compound that is presented for binding with a target molecule. In particular, the ratio between functionalized membrane-forming lipid and membrane-forming lipids is dependent on the identity of the functionalized membrane-forming lipid, and it can be as low as 1% or even lower and as high as 100% as NLPs have been successfully formed with 100% functionalized membrane-forming lipid such as DOGS-NTA-Ni (1,2-di-(9Z-octadecenoyl)-sn-glycero-3-[(N-(5-amino-1-carboxypentyl)iminodiacetic acid)succinyl] (nickel salt)). This suggests that NLPs can be formed with any percentage of functionalized membrane-forming lipid (from 0 to 100%), depending on the specific functionalized membrane-forming lipid used.

In general, assembly of NLPs according to the present disclosure can be accomplished with a wide range of ratios of total membrane-forming lipids to scaffold proteins. For example NLPs have been successfully formed with lipid to scaffold protein molar ratios of about 15:1 up to about 400:1. A typical assembly uses a lipid to scaffold protein molar ratio of about 100:1.

The term "anchor compound substrate" as used herein indicates a functional group capable to bind a corresponding functional group, herein also indicated as "anchor compound", presented on another molecule, and in particular on an antigen comprising molecule or an adjuvant molecule to be attached to the nanolipoprotein particle.

The term "bind", "binding", "conjugation" as used herein indicates an attractive interaction between two elements which results in a stable association of the element in which the elements are in close proximity to each other. If each element is comprised in a molecule the result of binding is typically formation of a molecular complex. Attractive interactions in the sense of the present disclosure includes both non-covalent binding and, covalent binding. Non-covalent binding as used herein indicates a type of chemical bond, such as protein protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities. An example of an electrostatic interaction includes using a charged lipid as the functional membrane lipid and binding an oppositely charged target molecule through electrostatic interactions.

Anchor compound substrates and corresponding anchor compound capable of binding through non-covalent binding include but are not limited to those listed in Table 1 below.

TABLE 1

Non-Covalent Interactions

| Anchor (on a target molecule) | Anchor substrate (on functionalized lipid within NLP bilayer) |
|---|---|
| Poly-histidine (2-10 residues) 2-10 residue polypeptide | Chelated metal cations $Ni^{2+}$, $Co^{2+}$, $Cu^{2+}$, $Zn^{2+}$ chelated on NTA, IDA |
| Poly-arginine (5-6 residues) 5-6 residue polypeptide | Negatively charged surface e.g. carboxylates, phosphates, sulfonates |
| Proteins | Biological tags |
| Avidin (Streptavidin, neutravidin) | Biotin |
| Glutathione S-transferase (GST) fusion proteins | Glutathione |
| Strep-Tactin | Strep-tag II |

A covalent bond is instead a form of chemical bonding that is characterized by the sharing of pairs of electrons between atoms, or between atoms and other covalent bonds. In short, attraction-to-repulsion stability that forms between atoms when they share electrons is known as covalent bonding. Covalent bonding includes many kinds of interaction, including σ-bonding, π-bonding, metal to non-metal bonding, agostic interactions, three-center two-electron bonds, and the like.

Anchor compound substrates and corresponding anchor compounds capable of binding through covalent binding include but are not limited to those listed in Table 2 below.

TABLE 2

Covalent Interactions

| Anchor (or anchor substrate) | Anchor substrate (or anchor) |
|---|---|
| Amine-reactive moieties Active esters (e.g. succinimidyl, tetrafluorophenyl) | Amines |
| Carbodiimide (+/−NHS)-Carboxylic acids | |
| Isothiocyanates | |
| Sulfonyl chlorides | |
| Dichlorotriazines | |
| Aryl halides | |
| Acyl azides | |

TABLE 2-continued

Covalent Interactions

| Anchor (or anchor substrate) | Anchor substrate (or anchor) |
|---|---|
| Thiol-reactive reagents<br>Maleimides (and derivatives)<br>Haloacetamides (e.g. iodoacetamide)<br>Pyridyldithio-propionate<br>Thiosulfates | Sulfhydryls |
| Azides<br>("Click Chemistry" -formation of 1,2,3-<br>triazol groups, ref. 7) | Acetylenes |
| Hydrazines/hydroxylamines/aromatic amines | Aldehydes and ketones |

Accordingly, exemplary functionalized membrane-forming lipids include, but are not limited to, chelated metal-bearing lipids, azide bearing lipids, maleimide bearing lipids, quaternary amine bearing lipids, carboxylate bearing lipids, propargyl bearing lipids, biotin bearing lipids, streptavidin and/or avidin bearing lipids, S-protein bearing lipids, and the like.

In some embodiments, binding or conjugation of the anchor compound can be performed by chelation. The term "chelation" as used herein indicates the binding or complexation of a bi- or multidentate ligand with a single metal ion. In particular, in some embodiments, the bi or multi-dentate ligand is part of the lipid and is capable of binding a metal ion. The ligands, which are often organic compounds, are called chelants, chelators, chelating agents, or sequestering agents. Chelating agents form multiple bonds with a single metal ion. The term "chelants" as used herein indicates a molecule that forms a stable complex with certain metal ions. Examples of chelating moieties include, but are not limited to, nitrilotriaceticacid (NTA), iminodiacetic acid (IDA), and diethylenetriamine penta-acetic acid (DTPA).

In the nanolipoprotein particle herein described the anchor substrate compound is attached to the functionalized membrane-forming lipid so that upon assembly of the functionalized membrane-forming lipid in the nanolipoprotein particle, the anchor substrate compound is presented on the nanolipoprotein particle. Similarly, the anchor compound is attached to an immunological molecule to be presented on said NLP.

In several embodiments the functionalized membrane-forming lipids are functionalized to present the anchor substrate compound on a hydrophilic moiety of the membrane-forming lipid to ensure presentation of the anchor substrate compound on a surface of the nanolipoprotein particle. The term "surface" as used herein indicates the exterior or upper boundary of a body or object. In particular with reference to the NLPs the term "surface" indicates they are defined by the discoidal faces. Surfaces of the NLPs form the hydrophilic portion of the NLP membrane bilayer.

Successful binding of an immunological agent to the NLP can be readily verified and quantified through a range of techniques that include but are not limited to centrifugal filtration, size exclusion chromatography, fluorescence correlation spectroscopy, cantilever-based sensing, force spectroscopy, fourier transform infrared spectroscopy, surface plasmon resonance, total internal reflection fluorescence, raman spectroscopy and additional techniques identifiable by a skilled person. In addition, binding specifically to the surface can be verified using atomic force microscopy and transmission electron microscopy and additional techniques identifiable by a skilled person.

The structure of nanolipoprotein particles herein described is illustrated in FIG. 1 which shows a schematic representation of an NLP assembly comprising a functionalized membrane-forming lipid according to some embodiments herein described.

As exemplified in the illustration of FIG. 1 panel A, purified starting components are provided that comprise a functionalized membrane-forming lipid (10), a membrane-forming lipid (20), and a scaffold protein (30). The functionalized membrane-forming lipid (10) comprises a hydrophobic moiety (11) and a hydrophilic moiety (12) and attached an anchor compound substrate (14) capable of binding to a corresponding anchor compound (41) presented on the immunological agent (40) of interest. In particular, the anchor compound substrate (14) is presented on the hydrophilic moiety (12) of the functionalized membrane-forming lipid (10). The functionalized membrane-forming lipid (10), the membrane-forming lipid (20), and the scaffold protein (30) are contacted for a time and under conditions to allow assembly of the NLP containing the functionalized membrane-forming lipid (100), shown in FIG. 1 Panel B. In particular, spontaneous interaction of purified scaffold proteins, e.g. apolipoproteins, and membrane-forming lipids under appropriate conditions results in formation of nanolipoprotein particles with the nanometer-sized dimensions that are herein identified as NLPs.

In the illustration of FIG. 1 Panel B the nanolipoprotein particle (100) formed by the assembly of the functionalized membrane-forming lipid (10), the membrane-forming lipid (20) and the scaffold protein (30) is configured to present the anchor compound substrate (14) on a surface of the nanolipoprotein particle. In particular, as shown in the illustration of FIG. 1 anchor compound substrate moieties are appended to the headgroups of the functionalized membrane-forming lipid, and are presented into solution.

The amount of anchor-substrate moieties on the NLP bilayer surface can be controlled by the input ratios of membrane-forming and functionalized anchor-substrate lipids during assembly, allowing control of immunological agent loading on NLP. Generally, if 10 molar percent of the total lipid used for an assembly is a functionalized membrane-forming lipid, then approximately 10 molar percent of the total lipid within the NLP lipid bilayer will be functionalized membrane-forming lipid. This has been verified in the case of NLPs prepared with 90 molar percent DMPC and 10 molar percent of DOGS-NTA-Ni. The feed ratio to incorporated ratio of the anchor substrate moiety can further be quantitatively assesses after completion of NLP assembly using normal phase and reverse phase high performance liquid chromatography and subsequent ratios can be adjusted to achieve the desired input ratio.

Although other reagents might be added according to the desired experimental design, no other reagents have to be added to impart functionality to the NLPs since the functionalized membrane-forming lipids containing the necessary reactive group for conjugation.

As schematically shown in FIG. 1 Panel C, an immunological agent (40) bearing the appropriate corresponding anchor compound (41) (an anchor compound able to bind and accordingly be defined as complementary to the anchor-compound substrate (14)) can be attached on the NLP bilayer surface of the NLP (100).

In particular, the immunological agent (40) and the nanolipoprotein (100) are contacted for a time and under conditions to allow binding of the anchor compound (41) with the anchor compound substrate (14), which depends on the conjugation chemistry between the anchor compound and the anchor substrate compound.

In particular, attachment of immunological agents to nanolipoprotein particles can be accomplished using any number of functionalization strategies and orientations. For example, using click chemistry, an acetylene-functionalized lipid can be conjugated with an azide-functionalized protein, or an azide-functionalized lipid can be conjugated with an acetylene-functionalized protein [Ref. 4].

In particular, the conjugation of azides with acetylenes (herein also indicated as click chemistry) can be achieved in buffered aqueous solution over a broad pH range for about 1 to about 24 hours to form a covalent 1, 2, 3 triazole. This reaction can be catalyzed by copper (I), typically introduced by addition of copper (II) in the presence of a reductant (e.g. ascorbic acid) to generate copper (I) in situ.

In other exemplary embodiments where attachment of a polyhistidine functionalized target molecule to a bivalent metal functionalized lipid is desired, conjugation of the polyhistidine anchor compound to the chelated metal ($Ni^{2+}$, $Co^{2+}$, $Cu^{2+}$, $Zn^{2+}$) anchor compound substrate (NTA or IDA) can be achieved over the course of an incubation ranging in time from about 5 minutes to about 2 hours at room temperature without the need of any additional components. According to this approach, no additional chelating agents (e.g. EDTA) are present in solution.

In other exemplary embodiments, where attachment of a poly-arginine functionalized immunological agent to a an anionic functionalized lipid is desired, conjugation of the poly-arginine anchor compound to an anionic surface anchor compound substrate can be achieved over the course of an incubation ranging in time from about 5 minutes to about 2 hours at room temperature without the need of any additional components.

In other exemplary embodiments where attachment of an immunological agent functionalized with a protein anchor, to a lipid functionalized with a cognate biological tag is desired, conjugation of the protein anchor compounds, e.g. avidin (and derivatives such as neutravidin and the like,), glutathione S-transferase (GST) and Strep-Tactin, to the cognate biological tag anchor compound substrates biotin, glutathione, and strept-tag II, respectively, can be achieved over the course of an incubation ranging in time from about 5 minutes to about 2 hours at room temperature without the need of any additional components.

In other exemplary embodiments, where attachment of an immunological agent to a functionalized lipid is performed through conjugation of active esters to amine, conjugation of the active esters to the amines is achieved in amine-free buffered aqueous solution at a pH of about 7.0 for about 1 to about 24 hours to form a covalent amide bond. Reaction can then be quenched upon addition of free amines at neutral to basic pH. No other reagents are needed to perform conjugation in those embodiments.

In other exemplary embodiments, where attachment of an immunological agent to a functionalized lipid is performed through conjugation of carboxylic acids to amine, conjugation of the carboxylic acids to the amines can be achieved by activating the carboxylic acid to an active ester, using commercially available reagents, e.g. N-hydroxysuccinimide (NHS). This can be accomplished by combining the NHS and a dehydrating agent (e.g. carbodiimides like 1-Ethyl-3-(3-dimethylaminopropyl)carbodiimide (EDC)) with the target carboxylic acid. The EDC reacts with the carboxylic moiety to form a transient amine-reactive O-acylisourea, whereby NHS converts the amine-reactive O-acylisourea to an amine-reactive NHS-ester. A covalent amide bond is can then be achieved in amine-free buffered aqueous solution at a pH of 7.0 for 1 to 24 hours. Reaction can then be quenched upon addition of free amines at neutral to basic pH.

In other exemplary embodiments where attachment of an immunological agent to a functionalized lipid is performed through conjugation of isothiocyanate to amine, conjugation of the isothiocyanates to the amines is achieved in amine-free buffered aqueous solution at a pH of about 7.0 for about 1 to about 24 hours to form a covalent thiourea. Reaction can then be quenched upon addition of free amines at neutral to basic pH. According to this approach, no other reagents are needed to obtain conjugation.

In other exemplary embodiments where attachment of an immunological agent to a functionalized lipid is performed through conjugation of maleimides (and maleimide derivatives) to sulfhydryls, conjugation of the maleimides (and maleimide derivatives) to sulfhydryls can be achieved in thiol-free buffered aqueous solution at a pH between about 6.5 and about 0.5 for about 1 to about 24 hours to form a covalent thioether linkage. Maleimides can then be quenched at the completion of the reaction by the addition of free thiol. Reducing agents (e.g. tris(2-carboxyethyl)phosphine) may be used to produce free, reactive sulfhydryls, which may also be stabilized by the addition of ethylenediaminetetraacetic acid (EDTA).

In other exemplary embodiments, where attachment of an immunological agent to a functionalized lipid is performed through conjugation of haloacetamide to sulfhydryls, conjugation of the haloacetamides to the sulfhydryls can be achieved in thiol-free buffered aqueous solution at a pH of about 8.3 for about 1 to about 24 hours to form a covalent thioether linkage by nucleophilic substitution of the halogen with the thiol. According to this approach no other reagents are needed to achieve conjugation.

In other exemplary embodiments, where attachment of an immunological agent to a functionalized lipid is performed through conjugation of pyridil disulfides to sulfhydryls, conjugation of the pyridyl disulfides to the sulfhydryls can be achieved in thiol-free buffered aqueous solution over a broad pH range for about 1 to about 24 hours to form disulfide bonds. According to this approach no other reagents are needed to achieve conjugation.

In other exemplary embodiments, where attachment of an immunological agent to a functionalized lipid is performed through conjugation of thiosulfate to sulfhydryls, conjugation of thiosulfates with sulfhydryls can be achieved in thiol-free buffered aqueous solution over a broad pH range for 1 to 24 hours to form disulfide bonds. No other reagents are needed in those embodiments.

In all those exemplary embodiments, conjugation of the immunological agent with the functionalized NLP can be monitored using techniques/methods such as a range of techniques that include but are not limited to centrifugal filtration, size exclusion chromatography, fluorescence correlation spectroscopy, cantilever-based sensing, force spectroscopy founer transform infrared spectroscopy, surface plasmon resonance, total internal reflection fluorescence, raman spectroscopy and additional techniques identifiable by a skilled person. In addition, binding specifically to the surface can be verified using atomic force microscopy and transmission electron microscopy and additional techniques identifiable by a skilled person.

In some embodiments, attachment of one or more immunological agents in a same functionalized NLP can be performed using different anchor compounds and corresponding anchor substrate for a same NLP where the selection of compatible anchor/anchor substrate pair can be performed by the skilled person in view of the immunological agent(s) to be attached, the chemistry of the compounds involved and the experimental design.

In particular, compatibility of the anchor/substrate pair of choice with all the NLP components has to be considered in selecting a suitable NLP for attaching a target molecule of interest. For example, in some embodiments amine-based conjugation is not compatible with certain scaffold proteins. A skilled person will be able to identify and sort components according to a desired experimental design.

In some embodiments, the immunological agent presented on the NLP is or comprise an adjuvant. A schematic illustration of nanoparticles attaching an adjuvant through binding of an anchor compound with a corresponding anchor compound substrate is shown in FIG. 1, where the immunological agent is an adjuvant. In particular, in the illustration of FIG. 1, schematically shows the coupling of adjuvants to the surface of a functionalized NLP bilayer. NLPs assembled with a fraction of headgroup-functionalized lipids, providing a means of either covalently or noncovalently coupling the adjuvant to the surface of the NLP bilayer.

Figure 4:
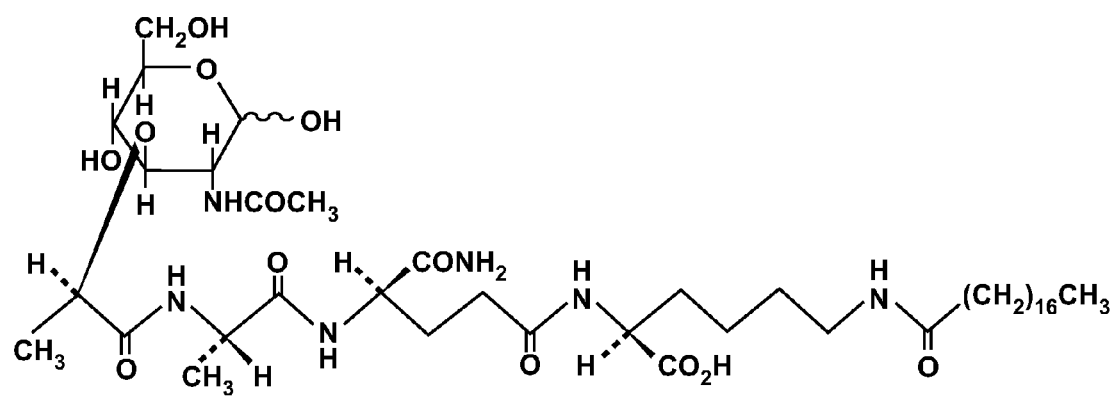
FIG. 4 shows the basic structure of amphipathic adjuvant muramyl dipeptide (MDP).
Figure 5:
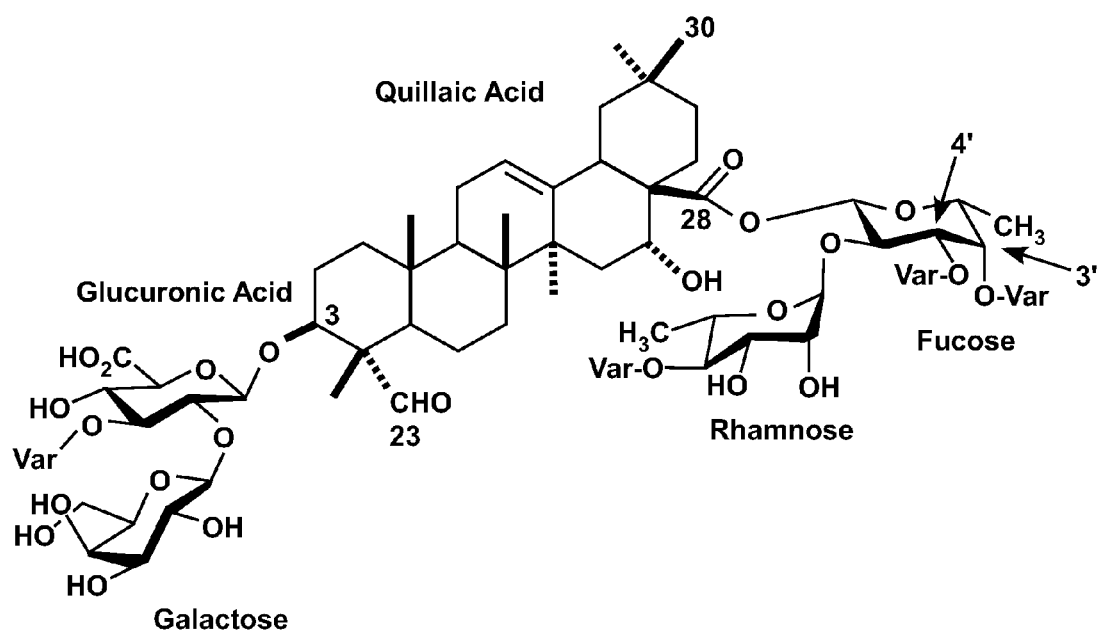
FIG. 5 shows the basic structure of an amphipathic saponin adjuvant.

Exemplary adjuvants that can be attached to an NLP herein described through anchor binding include, but are not limited to, immunostimulatory peptides (e.g. f-Met-Leu-Phe), muramyl dipeptide (including the analog muroctasin, see FIG. 4) [Refs. 7, 8 and 9], saponins (e.g. gylcosidic terpenes from *Qillaja saponaria*, see FIG. 5), toxins (e.g. tetanus, cholera), oligonucleotide CpG motifs (e.g. Agatolimod), immunostimulatory carbohydrates and polysaccharides, and immunostimulatory protein or peptide molecules (e.g. cytokines, chemokines, flagellin, and derivatives thereof).

In particular, in some embodiments, immunostimulatory NLPs herein described present saponins attached to the NLPs. Saponins are glycosylated triterpenoid compounds that have been shown to augment protective immune responses as well as exhibiting both antiviral and anticancer therapeutic efficacy. So in the case of NLP vaccine platforms, incorporation of selected saponins can provide a countermeasure that is not only protective as a vaccine but therapeutic as well.

In some embodiments, immunostimulatory NLPs herein described present oligonucleotides containing the nucleotide motif CpG attached to the NLP. Oligonucleotide comprising CpG motifs that have been demonstrated to have adjuvanting properties. These oligonucleotides are thought to be derived from microbial pathogens [Refs. 5 and 6]. Agatolimod, a synthetic 24-mer oligonucleotide, contains 3 CpG motifs (GTCGTT) and exhibits immunostimulatory activity by selectively targeting Toll-like receptor 9 (TLR9), activating dendritic and B cells and stimulating cytotoxic T cell and antibody responses. It is also active against tumor cells bearing certain tumor antigens, thus incorporating or promoting a therapeutic anticancer indication. The most active forms of these CpG-derived adjuvants are phosphorothioate analogs of DNA.

In some embodiments, immunostimulatory NLPs herein described present *Salmonella* flagellin attached to the NLP. *Salmonella* flagellin (FliC and related genes), has been previously utilized as both a carrier of antigen(s) and an adjuvant. Studies have suggested that flagellin remains at the site of inoculation for several hours prolonging presentation of antigenic epitopes to the immune system [Ref. 10] Recently, a 15-amino acid peptide (QTLIAIHTLAIRYAN-SEQ ID NO: 1) has been described as being an immunodominant T-cell epitope. This synthetic peptide has been shown to induce a protective cellular immune response in mice challenged with pathogen fungus *Paracoccioides brasiliensis*.

In some embodiments, the immunological agent presented on the NLP is or comprise an antigen. A schematic illustration of nanoparticles attaching an antigen through binding of an anchor compound with a corresponding anchor compound substrate is shown in FIG. 1, where the immunological agent is an antigen.

Exemplary antigens that can be attached to an NLP herein described through anchor binding include but are not limited to, viral proteins (or derivatives thereof), bacterial proteins (or derivatives thereof), fungal proteins (and derivatives thereof), proteins from eukaryotic organisms (and derivatives thereof), immunogenic carbohydrate moieties; signaling molecules (e.g. bacterial quorum sensing molecules), and other small molecule entities (e.g. plasticizers, dyes and drugs). Reference is made to the exemplary procedures of Examples 4 and 5, illustrating an exemplary immune response of an immunogen presented on a functionalized NLP.

In particular, in several embodiments immunostimulatory NLPs present at least one recombinant protein, including antigens such as the bacteriocin pesticin (Pst) from *Y. pestis*, the *Y. pestis* quorum sensing protein IsrG, the light chain of botulinum neurotoxin A, and envelope protein (Env) from West Nile virus (WNV). In those embodiments the recombinant proteins are anchored to the NLPs following attachment to the recombinant protein of anchor compounds such as a His-tag.

In several embodiments, immunostimulatory NLPs herein described can be formed with a variety of phospholipids including but not limited to: dimyristoylphospatidylcholine (DMPC), dioleoylphosphoethanolamine (DOPE), dioleoylphophatidylcholine (DOPC), dioleoylphosphoserine (DOPS), dioleoylphosphoserine (DOPS), dioleoyl-glycero-3-[(N-(5-amino-1carboxypentyl) iminodiacetic acid)succinyl] (DOGS-NTA).

In several embodiments, immunostimulatory NLPs herein described can be formed with apolipoproteins that include human ApoE4 22K and insect lipophorins from *Bombyx mori* and *Manduca sexta*, apoA-1, and ApoA-1 derivatives.

In several embodiments the functionalized membrane-forming lipid of the immunostimulatory NLP can include but is not limited to dioleoyl-glycero-3-[N-(5-amino-1-carboxypentyl)iminodiacetic acid)succinyl] (DOGS-NTA) and DOGS-NTA(Ni), 1,2-di-(9Z-octadecenoyl)-sn-glycero-3-phosphoethanolamine-N-[4-(p-maleimidophenyl)butyramide] (18:1 MPB PE), and 1,2-di-(9Z-octadecenoyl)-sn-glycero-3-phosphoethanolamine-N-(cap biotinyl) (sodium salt), and azido- and propargyl-modified lipids.

In particular, in some of those embodiments, where binding is performed by interaction with a chelated bivalent metal ion, the chelant is a modified lipid molecule, e.g. dioleoyl-glycero-3-[N-(5-amino-1-carboxypentyl)iminodiacetic acid)succinyl](DOGS-NitriloTriaceticAcid) and DOGS-NTA (bivalent metal ion) to which His-tagged proteins can be specifically and directly conjugated.

Embodiments based on the bivalent metal ion-chelating ability of NiNLPs allow conjugation of any (His)-tagged protein, opening the door to thousands of potential immunological agents. Bivalent metal ions comprise Ni and additional transition metals bound or chelated by poly-histidine sequences. Exemplary bivalent metal ions include but are not limited to $Co^{2+}$, $Ni^{2+}$, $Cu^{2+}$ and $Zn^{2+}$. Corresponding polyhistidine tags can be comprised at either one of the ends of the target molecule to be attached. For example a His-tag can be added at either the N- or C-terminus of recombinantely expressed proteins to enable rapid isolation and purification [Ref. 14].

In other embodiments, the membrane-forming lipid can be functionalized to contain an azide group that can react with an immunological agent (e.g. a protein) specifically modified to contain a propargyl group. The reaction product between the azide and acetylene group forms a 1,2,3-triazole moiety. The product of this cycloaddition reaction or "click chemistry" is a covalent association between the immunological agent and the NLP [Ref. 4].

Still in other embodiments, a thiol group is added to the immunological agent and is then reacted with a maleimide group presented on a functionalized membrane-forming lipid. Maleimide bearing lipids (functionalized anchor substrate lipid), are available commercially. In this case, an anchor-bearing immunological agent would be configured to present a free thiol group that could add to the maleimide moiety forming a covalent bond [Ref. 15].

In particular, metal chelating lipids, such as 1,2-di-(9Z-octadecenoyl)-sn-glycero-3-[(N-(5-amino-1-carboxypentyl)iminodiacetic acid)succinyl] (ammonium salt), and the like, that are suitable in forming NLPs herein described, are commercially available or synthesizable by a skilled person using techniques known in the art. In embodiments where metal chelating lipids are used in a functionalized NLP, the corresponding immunological agents are configured to contain a polyhistidine tag for conjugation. Attachment of a polyhistidine tag to the immunological agent can be achieved through molecular biological approaches and techniques identifiable by a skilled person.

Also negatively charged headgroup lipids, such as phosphatidic acid-, phosphatidylserine, phosphatidylglycerol-bearing lipids, and the like, that are suitable in forming NLPs herein described are commercially available or synthesizable by a skilled person using techniques known in the art. In embodiments where negatively charged headgroup lipids are used in a functionalized NLP, the corresponding immunological agents are configured to contain a polyarginine tag for conjugation. Attachment of a polyarginine tag to the immunological agent can be achieved through molecular biological approaches and techniques identifiable by a skilled person. Further, immunological agents that are inherently positively charged require no further modification.

Positively charged headgroup lipids, such as 1,2-di-(9Z-octadecenoyl)-3-trimethylammonium-propane (chloride salt), and the like, that are suitable in forming NLPs herein described are commercially available or synthesizable by a skilled person using techniques known in the art. In embodiments where positively charged headgroup lipids are used in a functionalized NLP, the corresponding target molecules are configured to contain an overall negative charge for conjugation sufficient to allow binding with the headgroup. In some of those embodiments the negatively charged immunological agents require no further modification to allow conjugation with the functionalized NLP.

Biotinylated lipids, such as 1,2-dihexadecanoyl-sn-glycero-3-phosphoethanolamine-N-(biotinyl)(sodium salt), and the like, that are suitable in forming NLPs herein described are commercially available or synthesizable by a skilled person using techniques known in the art. In embodiments where biotinylated lipids are used in a functionalized NLP, the corresponding immunological agents are configured to contain avidin (and/or derivatives thereof), via an additional biotin moiety.

Glutathione-derivatized lipids such as phosphatidylethanolamine-bearing lipid that are suitable in forming NLPs herein described be formed through coupling of glutathione to an appropriate lipid. In embodiments where glutathione-derivatized lipids are used in a functionalized NLP, the corresponding immunological agents are configured to contain a glutathione S-transferase fusion protein tag for conjugation. Attachment of a glutathione S-transferase fusion protein tag to the immunological agent can be achieved through molecular biological approaches and techniques identifiable by a skilled person.

Strep-tag II-derivatized lipids that are suitable in forming NLPs herein described can be formed through coupling of synthetic strept-tag II to an appropriate lipid, such as. phosphatidylethanolamine-bearing lipid, according to techniques identifiable by a skilled person In embodiments where glutathione-derivatized lipids used in a functionalized NLP, the corresponding immunological agents are configured to contain a compound such as Strep-Tactin, which is commercially available.

Amine-bearing lipids, such as phosphatidylethanolamine that are suitable in forming NLPs herein described are commercially available or synthesizable by a skilled person using techniques known in the art. In embodiments where amine bearing lipids are used in a functionalized NLP, the corresponding immunological agents are configured to contain an amine-reactive moiety, (e.g. active esters, isothiocyanates, sulfonyl chlorides, dichlorotriazines, aryl halides, acyl azides, and the like). Attachment of an amine reactive moiety to the immunological agent can be achieved through previously established coupling chemistries and techniques identifiable by a skilled person.

Carboxylic acid-bearing lipids, such as. 1,2-dihexadecanoyl-sn-glycero-3-phosphoethanolamine-N-(succinyl) (sodium salt), that are suitable in forming NLPs herein described are commercially available or synthesizable by a skilled person using techniques known in the art. In embodiments where carboxylic acids are used in a functionalized NLP, the corresponding immunological agents are configured to contain a reactive primary amine, e.g. lysine side chain presented on the immunological agent for binding with the carboxylic acid-bearing lipids.

Thiol-reactive lipids, such as 1,2-dihexadecanoyl-sn-glycero-3-phosphoethanolamine-N-[4-(p-maleimidophenyl) butyramide] (sodium salt), that are suitable in forming NLPs herein described are commercially available or synthesizable by a skilled person using techniques known in the art. In embodiments where thiol-reactive lipids are used in a functionalized NLP, the corresponding immunological agents are configured to contain a reduced sulfhydryl moiety, such as reduced cysteine residue.

Free sulfhydryl-bearing lipids, such as 1,2-Dipalmitoyl-sn-Glycero-3-Phosphothioethanol (Sodium Salt), that are suitable in forming NLPs herein described are commercially available or synthesizable by a skilled person using techniques known in the art. In embodiments where free sulfhydryl-bearing lipids are used in a functionalized NLP, the corresponding immunological agents are configured to contain thiol-reactive moieties, such as maleimides (and derivatives), haloacetamides, pyridyldithio-propionate, and thiosulfates.

Azide- and alkyne-bearing lipids that are suitable in forming NLPs herein described can be prepared from commercially available components that react with phosphatidylethanolamine-bearing lipids, e.g. 3-(azidotetra(ethyleneoxy)) propionic acid, succinimidyl ester and 3-propargyloxypropanoic acid, succinimidyl ester, respectively. In embodiments where azide- and alkyne-bearing lipids are used in a functionalized NLP, the corresponding immunological agents are configured to contain either an acetylene- or azide reactive group, respectively, to form a stable 1, 2, 3 triazole reaction product.

In any of the above embodiments, one or more additional same or different adjuvant and/or antigen can be attached to the immunostimulatory nanoparticle through binding the anchor compound-anchor substrate compound and/or through assembly of the additional adjuvant and/or antigen in the nanoparticle.

For example, in several embodiments, NLPs made from apolipoprotein and a mixture of DOGS-NTA (Ni) [1-50%] and DMPC, DOPC form nanoparticles containing nickel ions on the surface or face of the particle (Ni-NLPs). In some of those embodiments, protein conjugation between these Ni containing NLPs bind antigens formed by His labeled proteins (see Examples 1-3 wherein conjugation has been shown with particular reference the major envelope protein from West Nile Virus (WNV-Env).

According to the approach of the present disclosure, several chemically and/or biologically diverse immunological agents can be presented on an NLPs allowing assembly of customized immunostimulatory platforms comprising a combination of selected immunological agents immobilized on the surface of the lipid bilayer, obviating the need for a to contain a hydrophobic region for direct interaction with the hydrophobic core of the NLP bilayer.

In particular, in several embodiments, the NLPs herein described allow attachment of a hydrophilic immunological agent. The term hydrophilic immunological agent as used herein indicates an immunological agent that contain a large regions or structural domain that are charge-polarized and capable of hydrogen bonding, to the extent of enabling the molecule to dissolve more readily in water than in oil or other hydrophobic solvents. Exemplary hydrophilic immunological agents comprise CpGs, and protein/peptide adjuvants such as flagellin.

A schematic exemplary representation of an NLP comprising a self-assembled adjuvant is illustrated in FIG. 2. In particular, in the schematic representation of FIG. 2, showing direct incorporation into the NLP bilayer of an amphipathic adjuvant (50) that has a hydrophilic portion (52) and has a hydrophobic portion (51). The hydrophobic portion can either be intrinsic to the molecule (e.g. the $_{C16}$ alkane of muramyl dipeptide analog muroctasin, lipid moieties of MPLA) or can be synthetically appended (i.e. the adjuvant can be functionalized with a long chain fatty acid) to hydrophilic adjuvants. The latter approach would be appropriate for immunostimulatory peptides, saponins, and CpG-containing oligonucleotides, and the like. In either case, the adjuvant will be incorporated during the NLP assembly process, and will be partially embedded within the NLP bilayer.

As exemplified in the illustration of FIG. 2 Panel A, purified starting components are provided that comprise an amphipathic adjuvant (50), a membrane-forming lipid (20), and a scaffold protein (30). The amphipathic adjuvant (50) comprises a hydrophobic moiety (51) and a hydrophilic moiety (52). The hydrophobic moiety can be appended to a hydrophilic adjuvant using synthetic procedures identifiable by a skilled person or be naturally occurring. The amphipathic adjuvant (50), the membrane-forming lipid (20), and the scaffold protein (30) are contacted for a time and under conditions to allow assembly of the NLP.

In the illustration of FIG. 2 Panel B the nanolipoprotein particle (200) formed by the assembly of the amphipathic adjuvant (50), the membrane-forming lipid (20) and the scaffold protein (30) is configured to present the hydrophilic portion of the amphipathic adjuvant (52) on the surface of the nanolipoprotein particle. In particular, as shown in the illustration of FIG. 2 Panel B the hydrophilic portion of the amphipathic adjuvant is presented into solution.

The amount of amphipathic adjuvant on the NLP bilayer surface can be controlled by the input ratios of membrane-forming and functionalized anchor-substrate lipids during assembly, allowing control of adjuvant loading in the NLP. The feed ratio to incorporated ratio of the anchor substrate moiety can be quantitatively assesses after completion of NLP assembly using normal phase and reverse phase high performance liquid chromatography and subsequent ratios can be adjusted to achieve the desired input ratio.

Exemplary adjuvants that can be incorporated into an NLP herein described as a self-assembling component comprise; naturally occurring hydrophobic or amphipathic adjuvants, including but not limited to lipopolysaccharides (LPS), mono-phosphorylated Lipid A (MPLA), organic compounds (squalene, soribitol oleate esters), alpha-galactosyl ceramide, and lipotichoic acid (LTA), or hydrophilic adjuvants synthetically appended with a hydrophobic moiety, including microbial derivatives (e.g. CpG motifs, muramyl dipeptide (MDP), flagellin), plant derivatives (e.g. saponins), and immunostimulatory proteins (e.g. cytokines, toxins, and derivative peptides), and immunostimulatory carbohydrates and polysaccharides.

In particular, in some embodiments, immunostimulatory NLPs herein described present MPLA alone or in combination with additional adjuvants. MLPA is a well established adjuvant that has been shown to induce both cellular and humoral immune responses. MPLA is a low toxicity derivative of a bacterial cell wall component, lipopolysaccharide (LPS) [Ref. 11 and 12]. Chemically synthesized MPLA has been used successfully in subunit vaccine formulations, as epitomized by HPV vaccine such as, Cervarix™, which is currently awaiting FDA approval.

Exemplary antigen that can be attached to an NLP herein described through as a self assembling component comprise gp120 of Human Immunodeficiency Virus, bacterial cell surface proteins, such as M proteins of *Streptococcus pyogenes* invasin of *Yersinia pseudotuberculosis*, and fimbrillin of *Porphryomonas gingivalis*, envelope glycoproteins of Herpes simplex virus or measles virus, hemagglutinin ligand of influenza virus or parainfluenza virus. antigens of *Salmonella typhi, Salmonella choleraesuis, Salmonella enteritidis* and additional antigens identifiable by a skilled person.

According to the approach of the present disclosure, several, chemically and/or biologically diverse immunological agents can be presented on an NLPs allowing assembling of customized immunostimulatory platforms comprising a combination of selected immunological agents immobilized on the surface of the lipid bilayer, obviating the need for a to contain a hydrophobic region for direct interaction with the hydrophobic core of the NLP bilayer.

In particular, in several embodiments, the NLPs herein described allow attachment of a hydrophilic immunological agent. The term hydrophilic immunological agent as used herein indicates an immunological agent that contain a large regions or structural domain that are charge-polarized and capable of hydrogen bonding, to the extent of enabling the molecule to dissolve more readily in water than in oil or other hydrophobic solvents.

In any of the above embodiments, one or more additional same or different adjuvant and/or antigen can be attached to the immunostimulatory nanoparticle through binding the anchor compound-anchor substrate compound and/or through incorporation of an amphipathic adjuvant into the nanoparticle during self-assembly The structure of nanolipoprotein particles herein described is illustrated in FIG. 3, which shows a schematic representation of an NLP assembly comprising an amphipathic adjuvant and a functionalized membrane-forming lipid according to some embodiments herein described.

Figure 3:
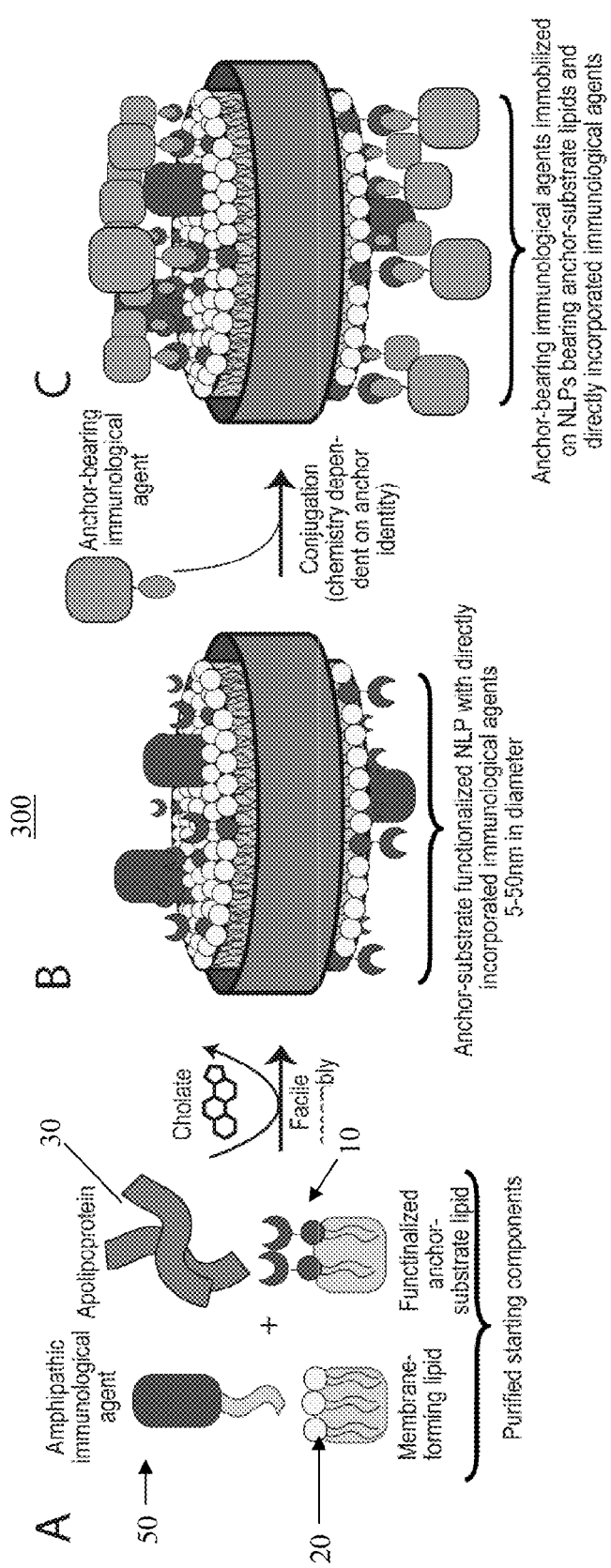
FIG. 3 shows a schematic illustration of assembly of a nanolipoprotein particle comprising both an amphipathic adjuvant directly incorporated into the NLP lipid bilayer and a functionalized membrane-forming lipid bearing an anchor compound substrate, according to an embodiment here described. Immunological agents bearing complementary anchor compounds can be immobilized onto the functionalized NLPs.

As exemplified in the illustration of FIG. 3 Panel A, purified starting components are provided that comprise a functionalized membrane-forming lipid (10), an amphipathic adjuvant (50), a membrane-forming lipid (20), and a scaffold protein (30). The functionalized membrane-forming lipid (10) comprises a hydrophobic moiety (11) and a hydrophilic moiety (12) and attached an anchor compound substrate (14) capable of binding to a corresponding anchor compound (41) presented on the immunological agent (40) of interest. In particular, the anchor compound substrate (14) is presented on the hydrophilic moiety (12) of the functionalized membrane-forming lipid (10). The amphipathic adjuvant (50) comprises a hydrophobic moiety (51) and a hydrophilic moiety (52). The hydrophobic moiety can be appended to a hydrophilic adjuvant using synthetic procedures identifiable by a skilled person or be naturally occurring. The functionalized membrane-forming lipid (10), the amphipathic adjuvant (50), the membrane-forming lipid (20), and the scaffold protein (30) are contacted for a time and under conditions to allow assembly of the functionalized membrane-forming lipid. In particular, spontaneous interaction of purified scaffold proteins, e.g. apolipoproteins, and membrane-forming lipids under appropriate conditions results in formation of lipoprotein particles with the nanometer-sized dimensions that are herein identified as NLPs.

In the illustration of FIG. 3 Panel B the nanolipoprotein particle (300) formed by the assembly of the functionalized membrane-forming lipid (10), an amphipathic adjuvant (50), the membrane-forming lipid (20) and the scaffold protein (30) is configured to present the anchor compound substrate (14) and the hydrophilic portion of the amphipathic adjuvant on the surface of the nanolipoprotein particle. In particular, as shown in the illustration of FIG. 3 Panel B, the hydrophilic portion of the amphipathic adjuvant and the anchor compound substrate moieties (appended to the headgroups of the functionalized membrane-forming lipids) are presented into solution.

The amount of anchor-substrate moieties and amphipathic adjuvant on the NLP bilayer surface can be controlled by the input ratios of membrane-forming and functionalized anchor-substrate lipids during assembly, allowing control of immunological agent loading on NLP. The feed ratio to incorporated ratio of the anchor substrate moiety can be quantitatively assesses after completion of NLP assembly using normal phase and reverse phase high performance liquid chromatography and subsequent ratios can be adjusted to achieve the desired input ratio.

Additionally, in several embodiments, the NLPs herein described can be used to attach multiple (i.e. 2 or more) immunological agents on the lipid bilayer surface. More particularly, in several embodiments multiple copies of a same immunological agent can be attached to the NLP. This greatly opens the door for applications where multivalency of an immunological agent on a controllable, discrete, and characterizable nanoscale platform is desired or required.

An example of desirable multivalency is provided by certain embodiments wherein immunostimulatory NLPs herein described that are configured to present an immunogen attached through anchor binding on the NLP. In general, it is known and accepted that multiple molecules presented in a dense and/or patterned motif elicit maximal immune response. Accordingly, in several embodiments immunostimulatory NLPs are provided that present multiple copies of an antigen on the NLP, to provide a clustering of the antigen on the immunostimulatory NLP.

Furthermore, in NLPs herein described the chemical nature of the antigen or other immunological agent to be immobilized on the NLP is not limited to a hydrophobic molecule (e.g. membrane protein) as is the case with all prior art examples, and can now include protein, peptides, oligonucleotides, small molecules, carbohydrates, metal ions, etc.

In some embodiments, the immunostimulatory NLPs comprise a self-assembled amphipathic adjuvant (e.g. MPLA) and non-covalently conjugated antigen (His-tagged protein). This facilitates co-localization of both adjuvant and antigen which will enhance the immune response to the antigen. This is exemplified in Examples 8 and 9.

In some embodiments, the immunostimulatory NLPs comprise a covalently conjugated hydrophilic adjuvant (e.g. thiolated CpG oligonucleotide adjuvants). This facilitates the clustering of a single adjuvant for enhanced stimulation of the immune system. This is exemplified in Examples 10 and 11.

In some embodiments, the immunostimulatory NLPs comprise two self-assembled amphipathic adjuvants (e.g. MPLA and αGalCer). The colocalization of two adjuvants provides a means of stimulating the immune system through two independent pathways. This is exemplified in Example 12.

In some embodiments, the immunostimulatory NLPs comprise a self-assembled amphipathic adjuvant (e.g. αGalCer) and a covalently-conjugated antigen (e.g. propargylated hemagglutinin). This facilitates co-localization of both adjuvant and antigen which will enhance the immune response to the antigen. This is exemplified in Examples 13 and 14.

In some embodiments, the immunostimulatory NLPs comprise a covalently-conjugated adjuvant (e.g. thiolated CpG oligonucleotide adjuvants) and a covalently-conjugated antigen (e.g. propargylated hemagglutinin). This facilitates co-localization of both adjuvant and antigen which will enhance the immune response to the antigen. This is exemplified in Examples 15 and 16.

In some embodiments, the immunostimulatory NLPs comprise a covalently-conjugated adjuvant (e.g. thiolated CpG oligonucleotide adjuvants) and a non-covalently-conjugated antigen (e.g. His-tagged protein). This facilitates co-localization of both adjuvant and antigen which will enhance the immune response to the antigen. This is exemplified in Examples 17 and 18.

In some embodiments, the formation of immunostimulatory NLPs herein described is amenable to the incorporation of multiple adjuvants, including compounds directed to enhance immune response e.g. non-human lipoproteins, bacterial peptides, DNA (e.g. CpG motifs), chemokines, cytokines, pattern-recognition receptors (PRR), lipids, polysaccharides, lipopolysaccharides, and the like; in general, agonists and immune stimulatory molecules, synthetic or natural, (known or unknown at this time) can be assembled in or on NLPs, providing for enhanced, specific, rapid immune stimulation at the site of NLP/antigen inoculation and spreading systemically.

In several embodiments, NLPs comprising an adjuvant such as microbial derivatives (e.g. CpG derivatives, MPLA), muramyl dipeptide derivatives (e.g. muroctasin), and any peptide or protein adjuvants (e.g. flagellin) can be incorporated into NLP directly to create an adjuvant NLP that can be used as an adjuvant or as a platform for subunit vaccine development with enhanced potency.

In particular, an adjuvant NLP according to the present disclosure can comprise single or multiple adjuvants, such as CpGs, MPLA, and cytokines. In some embodiments, an adjuvant NLP can be customized by including selected adjuvants in view of the desired effect based on the ability of different adjuvants to target different toll-like receptors (TLR) for immunostimulation (e.g. MPLA targets TLR 4, CpGs target TLR9, and flagellin targets TLR5). In some of these embodiments, the customization is performed in view of a specific vaccine formulation to be used in combination with the adjuvant NLP. The customization can be made to combine in the NLP only the adjuvants that are effective for the vaccine formulation of choice, since in some vaccine formulations only certain adjuvants are successful at enhancing the efficacy of the vaccine.

The adjuvant NLP can be used as a platform that can deliver multiple adjuvant molecules in a single vehicle that can be used as universal adjuvant for any type of vaccine formulation including but not limited to NLP-based vaccine formulations.

In particular, in some embodiments, immunogens of interest are directly conjugated to the adjuvant-incorporating NLPs, resulting in a vaccine platform where the immunogen and adjuvant are colocalized on the NLP. More particularly, the adjuvant NLP can be combined with an appropriate antigenic macromolecules, e.g. protein, carbohydrate, DNA, RNA, to originate a vaccine NLP construct via assembly performed either by: a) adding preformed MPLA-NLPs, including MPLA-NLPs, to a solution containing solubilized putative antigen molecules b) adding preformed MPLA-NLPs to a cell-free protein expression system for in vitro transcription/translation; or c) generating "in situ" both apolipoproteins and target membrane protein(s) by cell-free protein expression in the presence of phospholipid and MPLA mixtures described above.

In other embodiments, adjuvant NLPs can be used as a universal immune enhancer, These NLPs can be used in conjunction with any type immunogen can be administered with an antigen that is not directly conjugated to the NLP. In the latter case, the adjuvant-incorporating NLP can be used as a universal immune enhancer that can be used with any formulation of immunogen (including attenuated and killed organisms). In particular, adjuvant-incorporating NLP are amenable to the incorporation of multiple copies of the same or different types of adjuvants, opening the potential for specific tailored targeting to different toll-like receptors.

The immunostimulatory NLPs or the immunostimulatory composition herein described can also be administered to an individual alone or in combination with additional immunostimulatory agents to immunize the individual.

Figure 6:
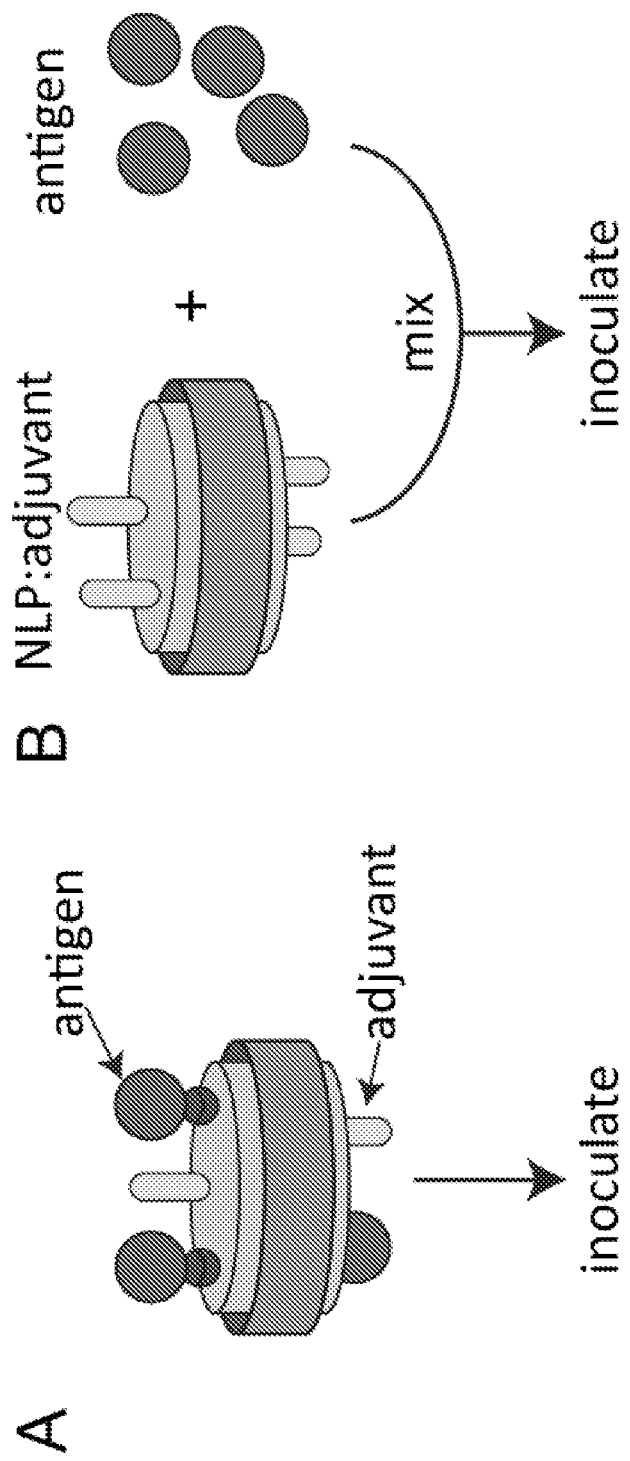
FIG. 6 shows a schematic illustration of two exemplary overall applications of NLPs bearing adjuvants according to some embodiments of the present disclosure. In particular, in the illustration of FIG. 6A, the NLPs incorporate both antigen and adjuvant molecules. This is amenable for adjuvants that can be incorporated into the NLP monolayer (amphipathic adjuvants) or adjuvants and/or antigens containing anchor compounds that can be immobilized to a NLP featuring functionalized membrane lipids bearing the complementary anchor compound substrates. These NLPs containing both adjuvant and antigen are used for inoculation. In the illustration of FIG. 6B, NLPs that incorporate only adjuvants (as described in Panel A). In some embodiments, prior to inoculation, these NLPs are mixed with vaccine components not amenable to NLP conjugation (e.g. attenuated whole cells or viruses). In some of these embodiments, the NLPs act to solubilize and deliver the adjuvant.

A schematic illustration of possible approaches to immunize an individual with the immunostimulatory NLPs herein described is illustrated in FIG. 6. FIG. 6 Panel A illustrates the incorporation of both antigen and adjuvant molecules in a vaccine-ready NLP. This is amenable for adjuvants that can be incorporated into the NLP monolayer (amphipathic adjuvants) or adjuvants and/or antigens containing anchor compounds that can be immobilized to a NLP featuring functionalized membrane lipids bearing the complementary anchor compound substrates. These NLPs containing both adjuvant and antigen are used for inoculation. FIG. 6 Panel B illustrates NLPs incorporating only adjuvants. Prior to inoculation, these NLPs are mixed with vaccine components not amenable to NLP conjugation (e.g. attenuated whole cells or viruses). In this case, the NLPs act to solubilize and deliver multiple copies of the same or different types of adjuvants.

Immunization can be effected by simple intramuscular injection in either the shoulder area or in the gluteus maximus hind muscular region. Particles could be delivered following solubilization in sterile normal saline solution, for example. Such immunizations would be subject to practices and methods approved by the US government Food and Drug Administration (FDA).

In particular, in some embodiments, the immunostimulatory NLPs that comprise at least one antigen can be used as vaccines that can be prepared rapidly and are relatively stable affording the desired protective immune response in accordance with attached immunogen.

For example, in some embodiments, the NLP construct conjugated with anchor-bearing antigen (e.g. His-tagged Env from WNV) is significantly more immunogenic than the soluble antigen alone, and can be used as a potential vaccine to protect against pathogen infection (e.g. WNV infection) when injected into an appropriate recipient animal without the aid or use of an adjuvant type carrier.

In some embodiments, the Lipid A component of lipopolysaccarhide (LPS) from gram negative bacteria can be included in this system with other phospholipids and lipids (DOGS-NTA) to form NLPs. These latter structures containing an incorporated membrane protein or with conjugated (e.g. His-tagged)-protein to become self-stimulating vaccine delivery platforms.

The term "vaccine" as used herein indicates a composition, and in particular a biological preparation, that establishes or improves immunity to a particular external pathogenic assault, or an inherent transformational incident resulting in a cancerous condition in mammals. Vaccines in the sense of the present description can be prophylactic, or therapeutic.

In particular, with respect to commercial vaccine preparation, binding of immunogens to NLPs is expected by the Applicants to both increase the potency of a vaccine antigen (reducing the need to produce higher amounts of immunogen, hence reducing costs), and minimize the need for addition of a non-specific adjuvants, as the addition of adjuvants also involve a higher cost. In several embodiments, immunostimulatory NLPs presenting antigens according to the present disclosure are safer and less expensive to produce even in embodiments wherein the immunostimulatory NLP does not present adjuvant. Additionally, in embodiments where an anchor bearing antigens (e.g. His-tagged immune stimulators) are added to an NLP platform presenting the corresponding anchor compound substrate on these NiNLPs can provide for safe stimulation of a more rapid and effective immune response (especially in the immunocompromised, young, and the elderly), further enhancing the utility of these vaccines in an emergency situation.

In several embodiments, the immunostimulatory NLPs presenting antigens alone or in combination with adjuvants conjugates encapsulate key requirements for vaccine formulation: non-virulence; immunostimulation; clustered antigen presentation; simple, rapid, inexpensive production; and the means to accommodate a wide range of select-agent antigens. Furthermore, adjuvant-bearing NLPs promote both humoral and cellular immune responses.

In some embodiments, the immunostimulatory NLP that presents one or more adjuvants only can be used as an adjuvant to be co-administered with adjuvants and/or antigens for example in vaccine compositions.

In several embodiments, the immunostimulatory particles are herein described and related compositions, methods and systems allow cost effective and rapid development of immunostimulatory compositions that are safe, enable immunization with multivalent/or broad-spectrum response and at the same time, are able to elicit a high levels protection following an adequate stimulation of an host immune response.

In several embodiments, the immunostimulatory particle, methods and systems herein described allow a rapid and cost effective development of immunogenic compositions against a broad spectrum of immunogenic molecules such as infectious agents, and in particular infectious agents for which a vaccine has not been developed, yet.

Additionally, in several embodiments, the immunostimulatory particle, methods and systems herein described provide an immunostimulatory particulate delivery/platform system that combined with anchor-bearing immunogenic molecules, such as but not limited to recombinant protein epitopes, provide a new approach to vaccines development.

Furthermore, in several embodiments, the immunostimulatory particle, methods and systems herein described allow preparation of an immunogenic composition in an amount of time that is considerably reduced compared with corresponding particles and systems of the art.

More particularly, in several embodiments, the immunostimulatory particle, methods and systems herein described allow rapid preparation of stable vaccine compositions capable of eliciting a desired protective immune response against any attached immunogenic molecule Additionally, in several embodiments, the immunostimulatory particle, methods and systems herein described can be used as particulate delivery systems, similar in size to certain pathogens while also enabling clustered, oriented and concentrated antigen presentation.

In several embodiments, the immunostimulatory particle, methods and systems herein described allow incorporation in the immunogenic particles of secondary additives to enhance immune response in the individual.

In some embodiments, any of the NLP herein described can be comprised in a composition together with a suitable vehicle. The term "vehicle" as used herein indicates any of various media acting usually as solvents, carriers, binders or diluents for an NLP comprised in the composition as an active ingredient.

In some embodiments, where the composition is to be administered to an individual the composition can be a pharmaceutical anti-inflammatory composition, and comprises an NLP and a pharmaceutically acceptable vehicle.

In some embodiments, an NLP can be included in pharmaceutical compositions (e.g. a vaccine) together with an excipient or diluent. In particular, in some embodiments, pharmaceutical compositions are disclosed which contain NLP, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb the NLP. Suitable excipients also include any substance that can be used to bulk up formulations with NLP to allow for convenient and accurate dosage. In addition to their use in the single-dosage quantity, excipients can be used in the manufacturing process to aid in the handling of NLP. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

In certain embodiments, compositions and, in particular, pharmaceutical compositions can be formulated for systemic administration, which includes parenteral administration and more particularly intravenous, intradermic, and intramuscular administration.

Exemplary compositions for parenteral administration include but are not limited to sterile aqueous solutions, injectable solutions or suspensions including NLP. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

The term "lyophilization" (also known as freeze-drying or cryodesiccation) indicates a dehydration process typically used to preserve a perishable material or make the material more convenient for transport. Freeze-drying works by freezing the material and then reducing the surrounding pressure and adding enough heat to allow the frozen water in the material to sublime directly from the solid phase to gas.

If a freeze-dried substance is sealed to prevent the reabsorption of moisture, the substance may be stored at room temperature without refrigeration, and be protected against spoilage for many years. Preservation is possible because the greatly reduced water content inhibits the action of microorganisms and enzymes that would normally spoil or degrade the substance.

Lyophilization can also causes less damage to the substance than other dehydration methods using higher temperatures. Freeze-drying does not usually cause shrinkage or toughening of the material being dried. In addition, flavors and smells generally remain unchanged, making the process popular for preserving food. However, water is not the only chemical capable of sublimation, and the loss of other volatile compounds such as acetic acid (vinegar) and alcohols can yield undesirable results.

Freeze-dried products can be rehydrated (reconstituted) much more quickly and easily because the process leaves microscopic pores. The pores are created by the ice crystals that sublimate, leaving gaps or pores in their place. This is especially important when it comes to pharmaceutical uses. Lyophilization can also be used to increase the shelf life of some pharmaceuticals for many years.

In pharmaceutical applications freeze-drying is often used to increase the shelf life of products, such as vaccines and other injectables. By removing the water from the material and sealing the material in a vial, the material can be easily stored, shipped, and later reconstituted to its original form for injection According to some embodiments, the functionalized membrane scaffold protein, the scaffold protein, the target molecule and/or any of the NLPs here described can be provided in a system.

In certain embodiments, an adjuvant and an NLP can also be comprised in a system to immunize an individual. In those embodiments, the system comprises: the immunostimulatory particle herein described and an adjuvant, the immunostimulatory particle and the adjuvant to be administered to the individual to immunize such individual.

The systems herein disclosed can be provided in the form of kits of parts. For example the target molecule can be included as a molecule alone or in the presence of lipids/detergents for transition in to nano-particles.

In a kit of parts, a functionalized membrane-forming lipid, the membrane-forming lipid, the target molecule, and/or scaffold protein are comprised in the kit independently, possibly included in a composition together with suitable vehicle carrier or auxiliary agents. For example a target molecule can be included in one or more compositions alone and/or included in a suitable vector. Also each of the membrane-forming lipid and functionalized membrane-forming lipid can be included in a composition together with a suitable vehicle carrier or auxiliary agent. Furthermore, the functionalized membrane-forming lipid and the target molecule can be included in various forms suitable for appropriate incorporation into the NLP.

Additional components can also be included and comprise microfluidic chip, reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (such as wash buffers and the like).

Further details concerning the identification of the suitable vehicle carrier or auxiliary agent of the compositions, and generally manufacturing and packaging of the kit, can be identified by the person skilled in the art upon reading of the present disclosure.

EXAMPLES

The methods and systems herein disclosed are further illustrated in the following examples, which are provided by way of illustration and are not intended to be limiting.

Example 1

Ni-NLP Assembly

Figure 7:
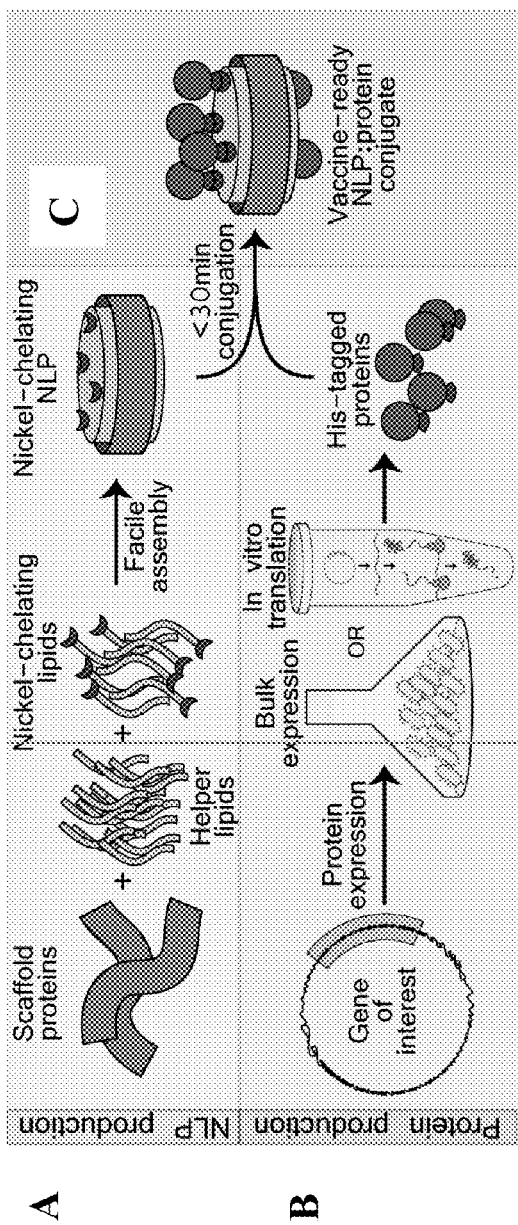
FIG. 7 shows an exemplary schematic of the process for assembling NLPs according to an embodiment herein described. In particular.

NiNLPs were assembled according to previously reported procedures [Ref. 5] and following the approach schematically illustrated in FIG. 7 Panel A.

Briefly, lipids (10% DOGS-NTA-Ni and 90% DMPC) were solubilized in chloroform and aliquoted into glass vials and solvent removed in vacuo. Lipids were then dissolved in TBS buffer (10 mM Tris, 150 mM NaCl) using sodium cholate. A typical NiNLP assembly contained E422K apolipoprotein, lipid, and 20 mM cholate. Samples were incubated at 23.8° C. for at least 1 hour and then dialyzed overnight against TBS. Separation by size exclusion chromatography (SEC) enabled purification of the NiNLPs. Pooled NiNLP containing fractions were concentrated using 50 k MWCO spin filters and analyzed by native gel electrophoresis, i.e. 4-20% Tris-glycine polyacrylamide gels followed by SyproRuby staining and fluorescent imaging. All assemblies were prepared at a 130:1 molar ratio of lipid to E4 22k.

Example 2

His-Tagged Target Protein Preparation

His-tagged immunogen protein were assembled according to previously reported procedures and following the approach schematically illustrated in FIG. 7 Panel B.

In particular, His-tagged proteins were prepared according to the approach illustrated in FIG. 7 Panel B, by recombinantly expressing a protein of interest with a His-tag. The His-tagged Env protein from WNV used in the experiments exemplified herein was produced by the use of a proprietary technology, but in principle many types of recombinant technologies identifiable by a skilled person could be used to produce this as well as other target protein of interest.

In particular, DNA expression systems could be utilized for its preparation. The ENV used in these studies was synthesized in a eukaryotic cell line (baby hamster kidney—BHK cells) using a patented non-cytopathic Venezuelan equine encephalitic virus replicon (VEErep) expression system [Ref. 1].

To ensure correct folding of Env, it was co-expressed in this VEErep with the WNV prM, since it has been shown that co-expression of these two flavivirus proteins is required for proper Env folding [Ref. 2]. The Env gene was further modified by removal of the nucleic acid sequences encoding the carboxy-terminal membrane binding domains of Env, and replacing these with a synthetic DNA sequence encoding a dual glycine spacer, and six histidine (His) residues. The VEErep containing this construct was also engineered to contain an antibiotic resistance gene (puromycin acetyl transferase). BHK cells transfected with the resulting VEErep were grown in the presence of puromycin (10 ug/ml) to produce BHK cell lines that constitutively expressed the VEErep and secreted the His-tagged truncated Env protein into their culture fluid. This Env protein has been reported to be a useful antigen for detecting antiviral responses to West Nile encephalitis vaccines [Ref. 3], and is used in this report both as the immunogen for NiNLP vaccine generation and as an enzyme-linked immunosorbent assay (ELISA) antigen for detecting vaccine responses to the of Env.

Example 3

NiNLP:His-Tagged Protein Assembly

NiNLPs assembled as exemplified in Example 1 above were conjugated with a target protein including an antigen prepared as exemplified in Example 2, according to the procedure schematically illustrated in FIG. 7 Panel C.

In particular, NiNLPs (0.1 ug/uL) were incubated with various concentrations of His-tagged proteins at room temperature for 45 minutes in a volume of 100 uL. A portion from each sample (60 uL) was subsequently filtered using 100 kDa Microcon molecular weight cut-off spin filters and washed three times with 100 uL of buffer. For control experiments, NiNLPs were pre-incubated in buffer containing 4 mM EDTA for 45 minutes at room temperature. For these samples, the wash buffer also contained 4 mM EDTA.

Figure 8:
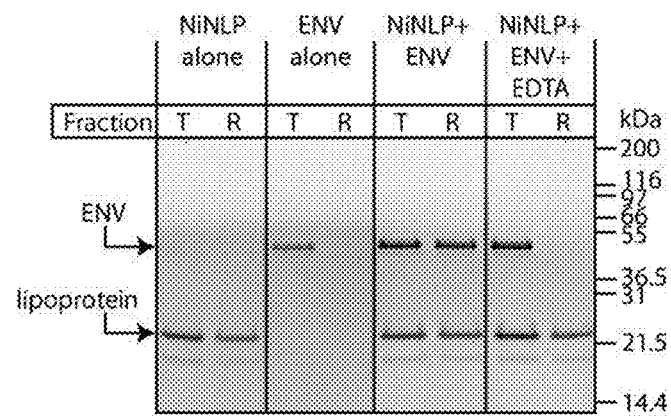
FIG. 8 shows analysis of an NLP platform with anchor-bearing immunogenic protein according to an embodiment herein described comprising in particular NiNLP:Env constructs. In particular.

The results are illustrated in FIG. 8. NiNLP:Env complexes show two bands corresponding to their constituent proteins (the scaffold protein E422K and the immobilized His-tagged protein, ENV). When EDTA is added, the complex formation is abrogated as expected following Ni removal by EDTA sequestration.

This His-tag:Ni interaction exemplified in this Example in connection with Example 1 and 2 was used to conjugate proteins to our NiNLPs, including a bacterial toxin subunit (BoNT), three bacterial cytosolic proteins of various sizes from *Y. pestis*, and the envelope protein (Env) from West Nile virus (WNV), effectively demonstrating the versatility of this conjugation approach. The immobilization of these His-tagged proteins on the NiNLP surface was verified by four independent techniques: size partitioning by centrifugal filtration, size exclusion chromatography (SEC), surface plasmon resonance (SPR) and atomic force microscopy (AFM).

Figure 9:
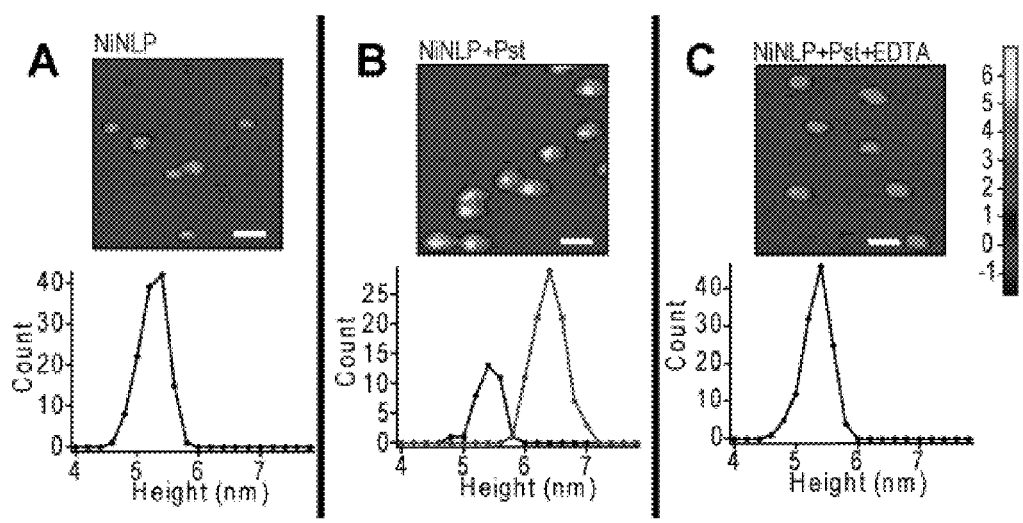
FIG. 9 shows atomic force micrographs demonstrating binding of His-tagged protein (pesticin) to NiNLPs.
Figure 10:
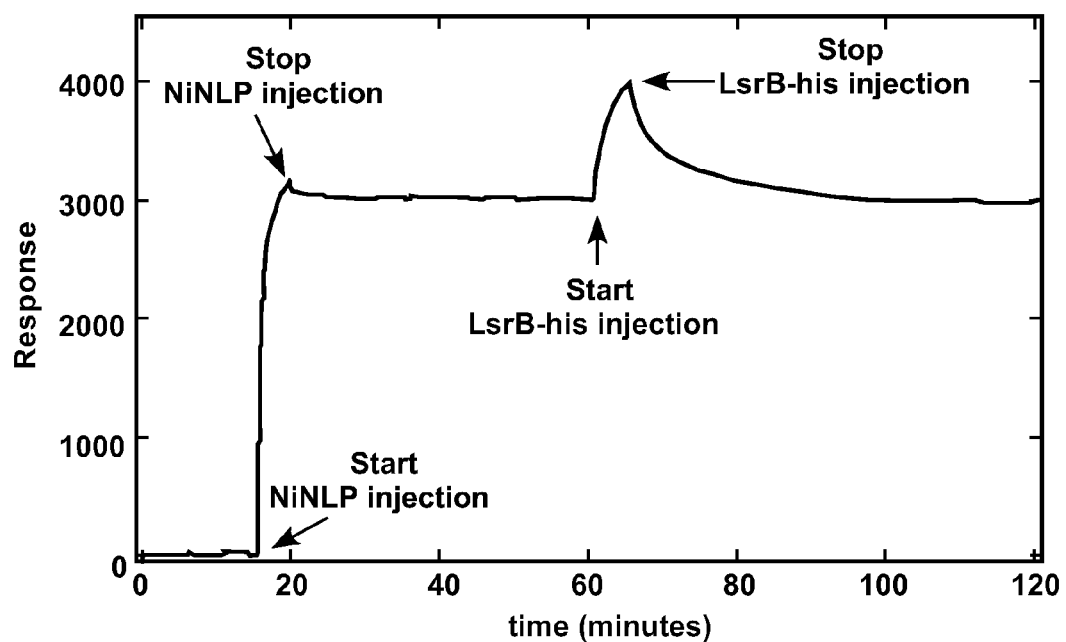
FIG. 10 shows results of conjugation as measured by Surface Plasmon Resonance (SPR). After NiNLP injection, absorption to the lipophilic SPR chip was monitored by change in SPR at the surface. Upon injection of His-tagged LsrB, a *Y. pestis* protein that is part of the ABC transporter complex, a second change in SPR was observed as indicated by the second peak in the SPR profile. After injection of LsrB was stopped, a slow and gradual decrease in the SPR signal was observed, indicative of LsrB disassociation from the NiNLP surface.

FIG. 9 illustrates ability of AFM to monitor the presence of antigens on the NiNLP surface, as demonstrated by the increase in NiNLP height upon incubation with His-tagged antigen. FIG. 10 shows the results of conjugation of his-tagged LsrB as measured by Surface Plasmon Resonance (SPR). After NiNLP injection, absorption to the lipophilic SPR chip was monitored by change in SPR at the surface. Upon injection of his-tagged LsrB, a *Y. pestis* protein that is part of the ABC transporter complex, a second change in SPR was observed as indicated by the second peak in the SPR profile. After injection of LsrB-his was stopped a slow and gradual decrease in the SPR signal was observed, indicative of LsrB-his unbinding.

NiNLP production for conjugation to His-tagged proteins performed according the procedure exemplified above and schematically illustrated in FIG. 7, allows performing NiNLP synthesis with control over constituents, size, and functional density. In particular, following the above procedure, conjugation of His-tagged protein to NiNLP can be accomplished in minutes, providing basis for Just-In-Time (JIT) vaccine development.

Example 4

Immune Response Associated with Administration of NiNLP-Immunogen Assemblies

To assess the immune response derived from NiNLP:Env constructs, samples were injected into groups of mice, each containing 5 outbred female 6-week-old Swiss Webster mice. NiNLP, Env and diluent (tissue culture media) were injected into their respective groups of mice and served as experimental controls. Collected antisera showed reactivity towards the WNV Env protein in two tests. In the first test, individual sera were diluted 1:100, and tested for their ability to react with WNV E protein in an ELISA assay [Ref. 3].

Figure 11:
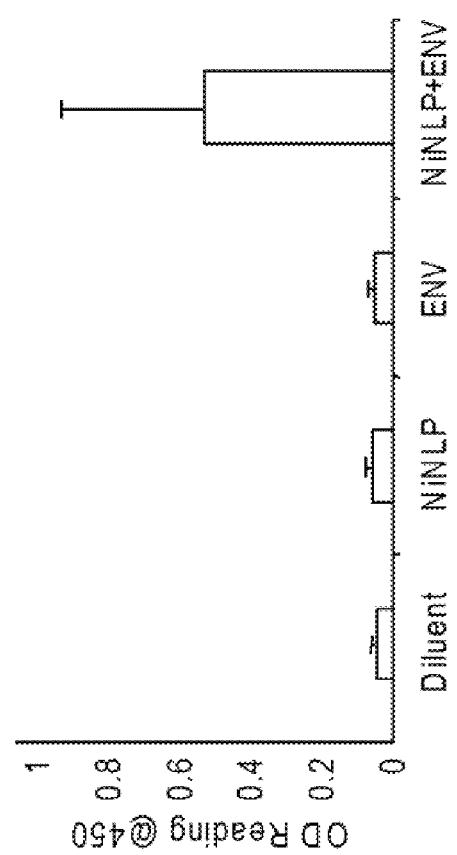
FIG. 11 shows a diagram illustrating the immune response following administration of immunostimulatory nanoparticles according to an embodiment herein described. In particular, the diagram illustrates ELISA data showing an immune response to the ENV target protein from mice collected 21 days post vaccination performed by intraperitoneal injection to inoculate the mice with NiNLP:ENV. ELISAs were performed on 1/100 dilutions of sera from all animals as previously described [Ref. 3]. Bars show the average ELISA OD readings, and extended bars show the standard deviations.

The results illustrated in FIG. 11, demonstrate immunity to Env in all sera collected from mice vaccinated with NiNLP: Env. Sera that were collected from mice vaccinated with NiNLP (alone) or Env (alone) displayed reactivity to Env indistinguishable from mice vaccinated with diluent (FIG. 11).

In a second series of experiments, WNV neutralization tests were performed by mixing pools of the 21-day post-vaccination sera collected from these mice with a WNV virus-like particle surrogate for fully infectious WNV [Ref. 3].

Figure 12:
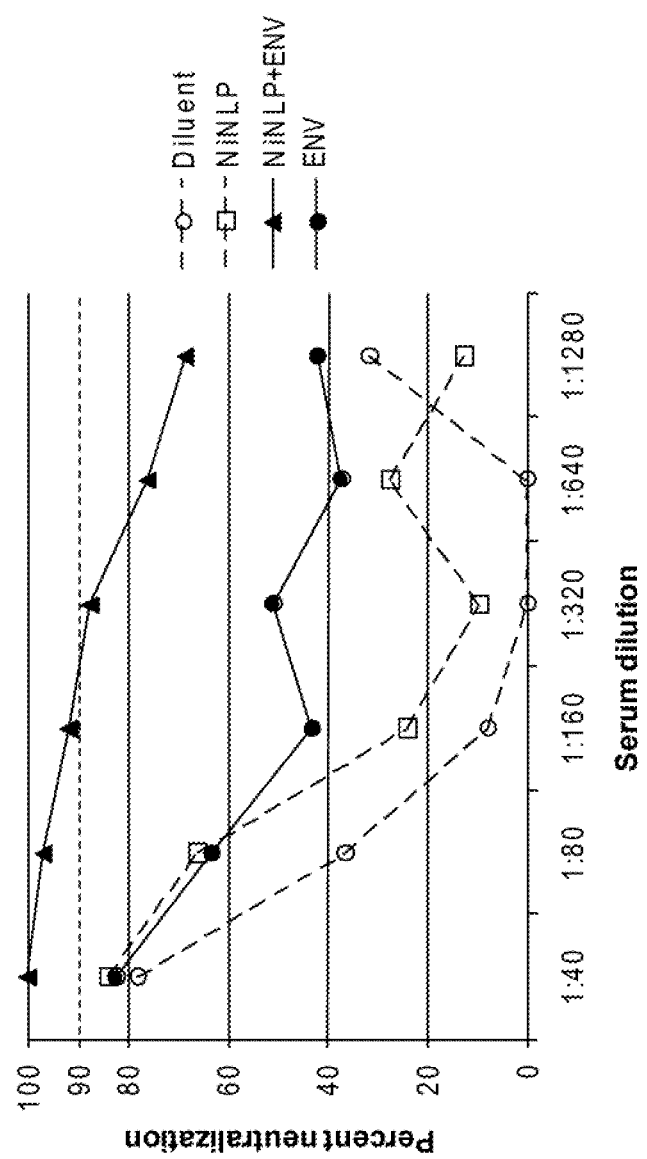
FIG. 12 shows a diagram illustrating neutralization of an immunogen following administration of an immunostimulatory nanoparticle according to an embodiment herein described. In particular, the diagram of FIG. 12 shows neutralization curves illustrating the ability of pooled sera from mice collected 21 days post vaccination with NiNLP:ENV to neutralize WNV virus-like particles (VLPs). Assays were performed on dilutions of sera from all animals as previously described [Ref. 3]. Data are expressed as % neutralization relative to VLPs incubated in the absence of any sera.

The results of this test, illustrated in FIG. 12, demonstrate that only the pool of sera from the mice that were vaccinated with NiNLP:Env displayed significant neutralizing activity. Specifically, these sera showed the ability to neutralize 90% of the input VLPs at a sera dilution of 1:160, whereas none of the other sera displayed detectable 90% neutralization at any serum dilution tested (FIG. 12).

When injected into mice, NiNLP:Env constructs gave rise to anti-Env antibody responses significantly better than Env alone, and NiNLP:Env preparation produced a WNV-neutralizing antibody response better than Env alone.

Example 5

Protection from Live Viral Challenge Following Administration of NiNLP-Antigen Assemblies The ability of NiNLP:Env to protect mice from virulent WNV challenge was performed as previously described [Ref. 3]. Briefly, at 5 weeks post vaccination, the animals treated as exemplified in Example 3 and related FIGS. 11 and 12, were injected by the intraperitoneal (IP) route with 1,000 focus-forming units of WNV, estimated to be approximately 10×50% lethal doses ($LD_{50}$) of virus in 9-week old animals, and observed daily for 21 days. Animals that appeared to be so ill that they would not survive until the next day were euthanized for animal welfare reasons, and recorded as having died the following day.

Figure 13:
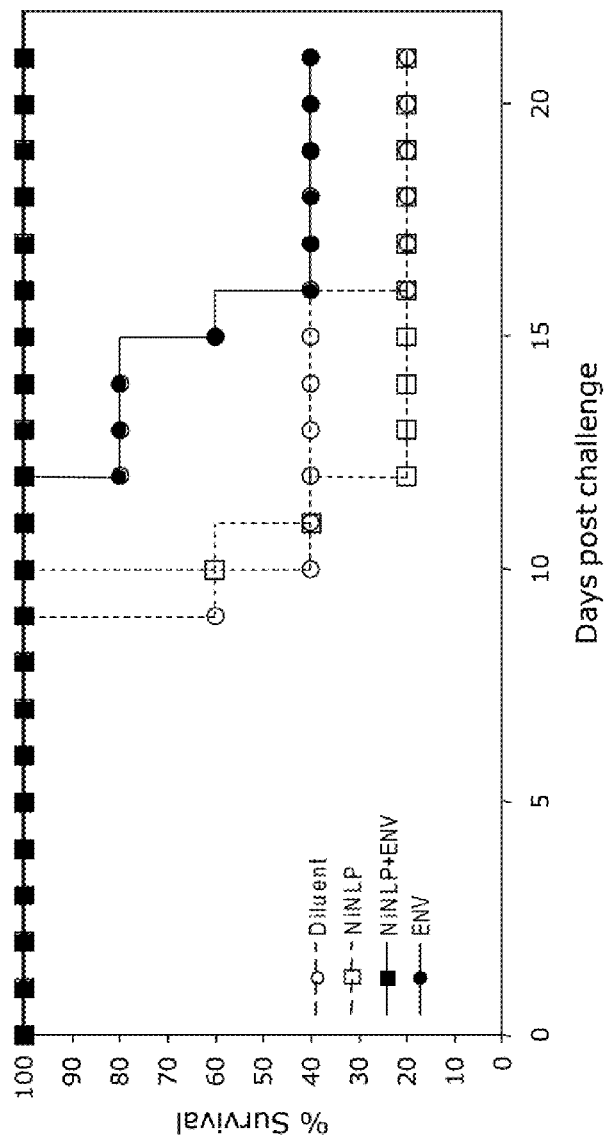
FIG. 13 shows a diagram illustrating protection from viral challenge following administration of immunogenic NiNLPs according to an embodiment herein disclosed. In particular, the diagram of FIG. 13 shows data related to mouse survival over the 21 day period following challenge with virulent WNV.

The data concerning surviving animals were plotted in the chart illustrated in FIG. 13. The survival curve shown in FIG. 13 demonstrated that all mice inoculated with NiNLP:Env survived to 21 days post challenge when the experiment was terminated. The control populations succumbed to infection with the exception of two animals the received Env protein, and one animal in each of the NiNLP (alone) or diluent groups.

When these animals were challenged by intra-peritoneal (IP) administration of live, fully infectious West Nile virus, 100% of the NiNLP:Env-vaccinated animals survived, whereas 60% of the animals vaccinated with Env alone died. At the day of experiment end (day 21) none of the animals remaining showed any signs of illness (lethargy, paralysis, ruffled fur), and all had a weight within 5% of challenge-day weight.

The approach outlined in the present example section is representative of a more general strategy wherein any protein with a His-tag can be used to generate a NLP-based construct in a matter of a few hours and can be administered to afford protective immunity. The approach offers one more advantage; since the NiNLP offers the ability to co-deliver immune stimulators (including, but not limited to: chemokines, cytokines, pattern-recognition receptor (PRR) agonists, or other immune stimulatory molecules, synthetic or natural, known or unknown at this time) similarly derivatized with a His-tag, providing for enhances, specific, rapid immune stimulation at the site of NiNLP/antigen delivery/uptake. Given the rapidity of preparation, applicants have coined the term JIT-vaccines; JIT comes from Just-In-Time moniker associated with well practiced manufacturing processes designed to be maximally productive and efficient while maintaining minimal inventory stock.

Applicants have successfully produced numerous NLPs varying in apolipoprotein (scaffold protein) identity and lipid composition. While the goal of NLP development focuses on the incorporation of membrane proteins within the lipid bilayer, the NLPs can also be used as a platform for the conjugation of any His-tagged protein. This is accomplished by introducing low amounts of nickel-chelating lipids during the formation process, resulting in the presentation of chelated nickel to an environment external to the lipid bilayer that is contained by the NLP itself. Applicants refer to these new NLP constructs as NiNLPs.

Applicants have used this His-tag:Ni interaction to conjugate proteins to our NiNLPs, including a bacterial toxin subunit (BoNT), three bacterial cytosolic proteins from *Y. pestis*, and the envelope protein (Env) from West Nile virus (WNV), effectively demonstrating the versatility of this conjugation approach. The immobilization of these His-tagged proteins on the NiNLP surface was verified by four independent techniques: size partitioning by centrifugal filtration, size exclusion chromatography (SEC), surface plasmon resonance (SPR) and atomic force microscopy (AFM).

Example 7

Protection from Antigens Challenge Following Administration of NiNLP-Antigen Assemblies at Various Concentrations This study has been repeated with larger groups of mice and different concentrations of antigen; the observations were consistent: NiNLP:Env constructs provided protection against WNV challenge. Single inoculations with 2.5 ug ENV antigen (in NiNLP:Env construct) provided greater than 90% protection against a live WNV challenge. Single inoculations with 0.5 ug ENV antigen (in NiNLP:ENV construct) provided 70% protection against a live WNV challenge. The NiNLP carrier alone offered no protection against the challenge, whereas the His-tagged Env protein alone provided only minimal protection against infection. These results demonstrate that NiNLPs are able to enhance the immune response to a conjugated antigen, and suggest that this approach can be more universally applied to recombinant antigens from a diverse range of pathogens.

Example 8

Figure 14:
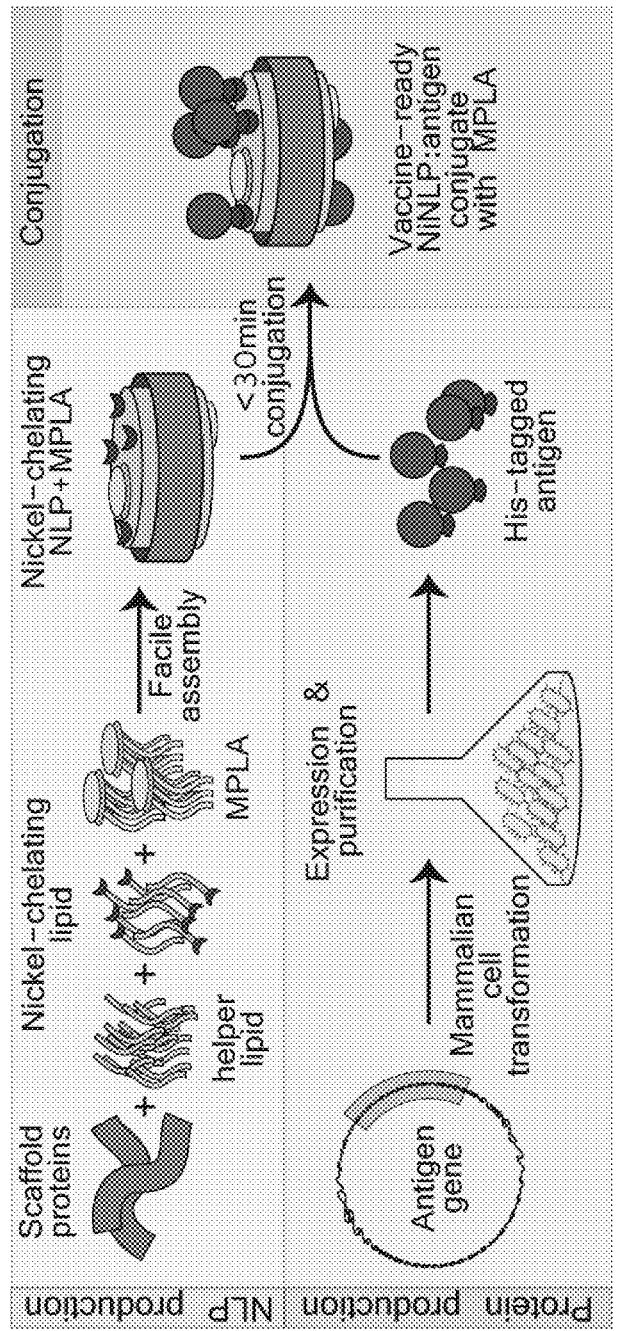
FIG. 14 shows a schematic illustration of assembly of a nanolipoprotein particle comprising a functionalized membrane-forming lipid and the amphipathic adjuvant MPLA according to an embodiment here described.

Preparation of NLPs Containing Self-Assembled Adjuvant (MPLA) and Functional Anchor Compound Substrate Lipid for Non-Covalent Antigen Attachment (Nickel-Chelating Lipid): MPLA-NiNLP MPLA-Ni-NLPs can be assembled in a similar manner to NiNLPs described in Example 1 (see FIG. 14).

To demonstrate MPLA incorporation into NiNLPs, we prepared seven NiNLP assemblies in the presence of various concentrations of MPLA (0, 0.1, 0.25, 0.5, 1.0, 2.5 and 5.0 mole percent of total lipid). Briefly, lipids (DMPC and DOGS-NTA-Ni at a 65:35 ratio) were solubilized in chloroform and aliquoted into glass vials. MPLA, also in chloroform, was added to the lipid solutions. The lipid-MPLA solutions were dried as a thin film. Lipid and MPLA were subsequently solubilized in TBS by vortexing, then sonication to form small unilamellar vesicles. Subsequently, cholate was added to a final concentration of 20 mM cholate.

Scaffold protein was added to the solubilized MPLA-lipid and allowed to incubate for 1 hour at room temperature. After thorough dialysis to remove residual cholate, the assemblies were analyzed by size exclusion chromatography (see FIG. 15).

Fractions collected by size exclusion chromatography were analyzed for MPLA content using an immunoblot. A small volume from each fraction was spotted onto a PVDF membrane, which was subsequently blocked with 5% BSA to prevent any nonspecific interaction in subsequent steps. The membrane was then incubated with a primary antibody against MPLA for 1 hour in a 1% BSA supplemented buffer. After washing, the blot was incubated with a fluorescently labeled secondary antibody against the primary antibody for 30 minutes. After additional washing steps, the blot was analyzed for fluorescence. Fluorescence intensity was quantified by densitometry.

Figure 15:
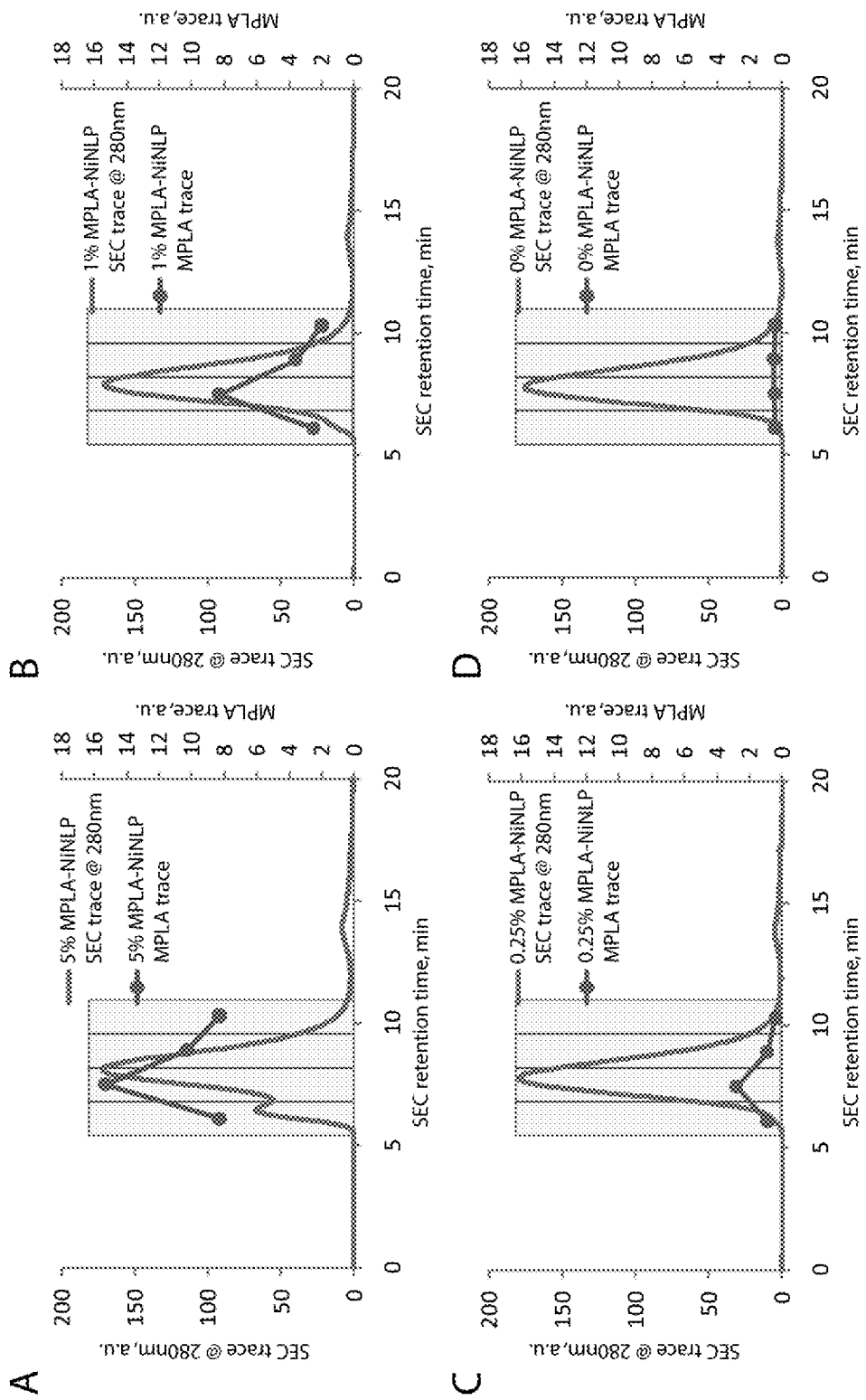
FIG. 15 shows the results of assemblies of nanolipoprotein particles with the amphipathic adjuvant monophosphorylated Lipid A (MPLA). Assemblies of NLPs with apoE422K, DMPC, and DOGS-NTA-Ni were conducted in the presence of A) 5, B) 1, C) 0.25, and D) 0% MPLA (molar ratio of total lipid). Assembled NLPs were purified by SEC (solid trace). The collected SEC fractions (shaded regions) were spotted onto a PVDF membrane, blocked with BSA, and probed with a primary antibody specific for MPLA. A fluorescently labeled secondary antibody against the primary antibody was used for detection. Fluorescence signals were quantified by densitometry (circles).
Figure 16:
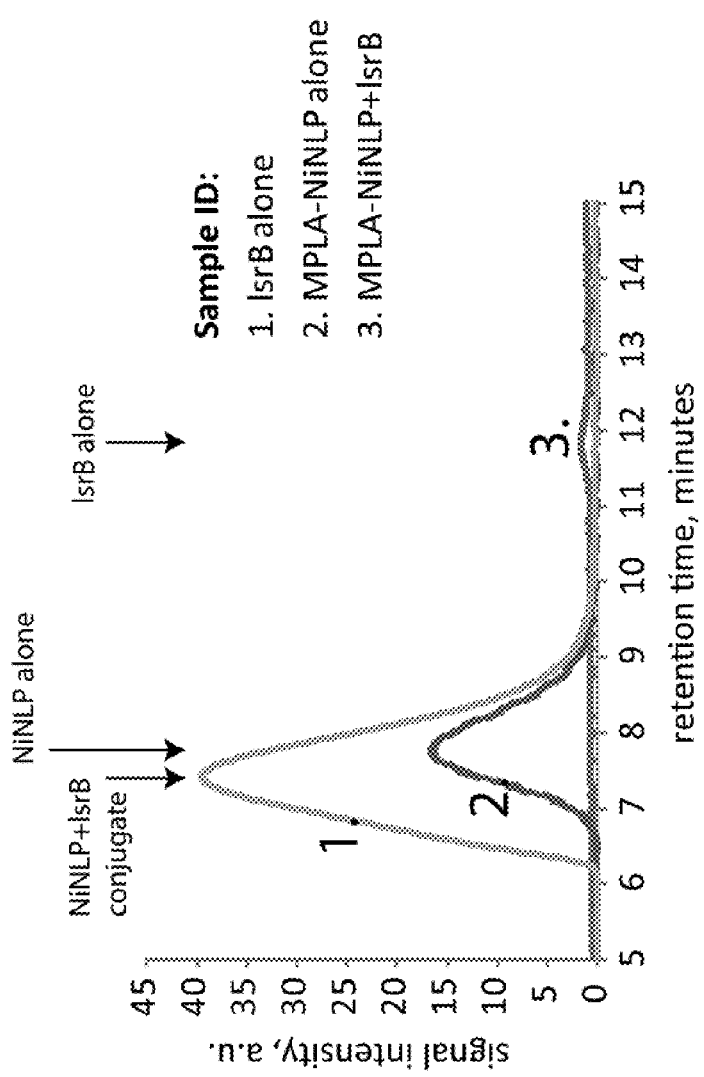
FIG. 16 shows the successful conjugation of the His-tagged antigen lsrB to MPLA-containing NiNLPs (MPLA-NiNLP). Sample were incubated at room temperature for 30 minutes, and subsequently analyzed by analytical size exclusion chromatography. LsrB alone (trace 1.) eluted at 11.8 minutes. MPLA-NiNLP alone (trace 2.) eluted at 7.8 minutes. LsrB incubated with MPLA-NiNLP resulted in a complex eluting at 7.4 minutes. Larger complexes display smaller retention times, indicating that the MPLA-NiNLP:lsrB complex is larger than MPLA-NiNLP alone.

MPLA was found to be present in fractions corresponding to the NLP fractions (FIG. 15). The concentration of MPLA in the particle was increased as the amount of MPLA in the initial assembly was increased from 0 to 5% (FIG. 15). These results indicate that MPLA can be successfully incorporated into the functional NLPs featuring 35% DOGS-NTA-Ni.

Example 9

His-Tagged Antigen Conjugation to MPLA-NiNLP

MPLA-NiNLPs as exemplified in Example 8 were conjugated with the His-tagged antigen lsrB.

To verify that MPLA-containing NiNLPs can bind a His-tagged protein, the MPLA-NiNLPs were incubated for 30 minutes with the His-tagged *Y. pestis* protein lsrB. To determine successful conjugation, lsrB alone, MPLA-NiNLPs alone, and MPLA-NiNLP:lsrB samples were analyzed by analytical SEC. Analytical SEC separates samples by size, whereby larger complexes are eluted from the column earlier than smaller complexes. Hence, conjugation of his-tagged lsrB to MPLA-NiNLP will result in an earlier elution time since it larger than both MPLA-NiNLP alone and lsrB alone, as shown in FIG. 16. LsrB alone has a retention time of 11.8 minutes. MPLA-NiNLP has a retention time of 7.8 minutes. MPLA-NiNLP:lsrB demonstrates a shift in retention time to 7.4 minutes and is also of higher signal intensity, which is also evidence of lsrB conjugation to MPLA-NiNLP.

Example 10

Example of NLP Preparation Containing One Functional Anchor Compound Substrate Lipid for Covalent Adjuvant Attachment (Maleimide Lipid)

Maleimide-NLPs were assembled in a similar manner to NiNLPs described in Example 1.

Briefly, lipids (10% 1,2-dihexadecanoyl-sn-glycero-3-phosphoethanolamine-N-[4-(p-maleimidophenyl)butyramide] (sodium salt) and 90% DMPC) were solubilized in chloroform and aliquoted into glass vials and solvent removed in vacuo. Lipids were then dissolved in TBS buffer (10 mM Tris, 150 mM NaCl) using sodium cholate. A typical Maleimide-NLP assembly contained E422K apolipoprotein, lipid, and 20 mM cholate. Samples were incubated at 23.8° C. for at least 1 hour and then dialyzed against TBS. Separation by size exclusion chromatography (SEC) enabled purification of the Maleimide-NLPs. Pooled Maleimide-NLP containing fractions were concentrated using 50 k MWCO spin filters and analyzed by native gel electrophoresis, i.e. 4-20% Tris-glycine polyacrylamide gels followed by SyproRuby staining and fluorescent imaging. Typical assemblies were prepared at a 130:1 molar ratio of lipid to E4 22k.

Example 11

Prophetic Example of Covalent Conjugation of an Adjuvant (Thiolated CpG Oligonucleotide) to Maleimide-NLPs Maleimide-NLPs as exemplified in Example 11 can be conjugated with thiolated CpG oligonucleotide adjuvants.

In particular, commercially available thiolated CpG oligonucleotide adjuvants (e.g. HS-CpG, 22 nucleotides in length with 5' sulfhydryl) are reduced in 5 mM (tris(2-carboxyethyl) phosphine) (TCEP) in TBS buffer (10 mM Tris, 150 mM NaCl). Free TCEP can be removed using a desalting column. The reduced, thiolated oligonucleotide is then incubated with the Maleimide-NLPs at range of molar ratios between 2 and 50 for 2 hours. Conjugation can then be monitored by SEC and/or native gel electrophoresis.

Example 12

Prophetic Example of NLP Preparation Containing Two Different Self-Assembled Adjuvants (MPLA and αGalCer)

MPLA/αGalCer-NLPs can be assembled in a similar manner to NiNLPs described in Example 1.

Briefly, lipids (96% DMPC, 1% MPLA, and 3% αGalCer) are solubilized in chloroform and aliquoted into glass vials.

The lipid solution is dried as a thin film. Lipids are subsequently solubilized in TBS by vortexing, then sonicated to form small unilamellar vesicles. Subsequently, cholate is added to a final concentration of 20 mM cholate. A typical MPLA/αGalCer-NLP assembly will contain E422K apolipoprotein, lipid, and 20 mM cholate. Samples are incubated at 23.8° C. for at least 1 hour and then dialyzed overnight against TBS. Separation by size exclusion chromatography (SEC) enabled purification of the MPLA/αGalCer-NLPs. Pooled MPLA/αGalCer-NLP containing fractions are analyzed by native gel electrophoresis, i.e. 4-20% Tris-glycine polyacrylamide gels followed by SyproRuby staining and fluorescent imaging. Typical assemblies are prepared at a 130:1 molar ratio of lipid to E4 22k.

Example 13

Prophetic Example of NLP Preparation Containing One Self-Assembled Adjuvant (αGalCer) and One Functional Anchor Compound Substrate Lipid for Covalent Antigen Attachment (azido-DMPE Lipid)

Azido/αGalCer-NLPs can be assembled in a similar manner to NiNLPs described in Example 1.

Briefly, 2-dimyristoyl-sn-glycero-3-phosphoethanolamine (DMPE) is reacted with 3-(azidotetra(ethyleneoxy)) propionic acid, succinimidyl ester to form an azido-functionalized lipid (Azido-DMPE). Lipids (3% αGalCer, 10% Azido-DMPE and 87% DMPC) are solubilized in chloroform and aliquoted into glass vials and solvent removed in vacuo. Lipids are then dissolved in TBS buffer (10 mM Tris, 150 mM NaCl) using sodium cholate. A typical Azido/-αGalCer NLP assembly will contain E422K apolipoprotein, lipid, and 20 mM cholate. Samples are incubated at 23.8° C. for at least 1 hour and then dialyzed overnight against TBS. Separation by size exclusion chromatography (SEC) enabled purification of the Azido/-αGalCer NLPs. Pooled Azido/αGalCer NLPs containing fractions are analyzed by native gel electrophoresis, i.e. 4-20% Tris-glycine polyacrylamide gels followed by SyproRuby staining and fluorescent imaging. Typical assemblies are prepared at a 130:1 molar ratio of lipid to E4 22k.

Example 14

Prophetic Example of Covalent Conjugation of an Antigen (Propargylated Hemagglutinin) to Azido/αGalCer-NLPs Azido/αGalCer-NLPs as exemplified in Example 10 can be conjugated with propargylated hemagglutinin In particular, hemagglutinin is propargylated using commercially-available 3-propargyloxypropanoic acid-succinimidyl ester. The alkyne-containing antigen is incubated with the Azido/αGalCer-NLPs in TBS buffer (10 mM Tris, 150 mM NaCl) supplemented with ascorbic acid and copper (II) sulfate for 1 hour. Reaction product is purified and monitored by SEC and/or native gel electrophoresis.

Example 15

Prophetic Example of NLP Preparation Containing Two Different Functional Anchor Compound Substrate Lipids (Maleimide- and Azido-Lipids) for Covalent Attachment of Adjuvant (Thiolated CpG Oligonucleotide) and Antigen (Propargylated Hemagglutinin)

Maleimide/azido-NLPs were assembled in a similar manner to NiNLPs described in Example 1.

Briefly, 2-dimyristoyl-sn-glycero-3-phosphoethanolamine (DMPE) is reacted with 3-(azidotetra(ethyleneoxy)) propionic acid, succinimidyl ester to form an azido-functionalized lipid (Azido-DMPE). Lipids (5% 1,2-dihexadecanoyl-sn-glycero-3-phosphoethanolamine-N-[4-(p-maleimidophenyl)butyramide] (sodium salt), 5% Azido-DMPE and 90% DMPC) are solubilized in chloroform and aliquoted into glass vials and solvent removed in vacuo. Lipids are then dissolved in TBS buffer (10 mM Tris, 150 mM NaCl) using sodium cholate. A typical Maleimide/azido-NLP assembly contains E422K apolipoprotein, lipid, and 20 mM cholate. Samples are incubated at 23.8° C. for at least 1 hour and then dialyzed against TBS. Separation by size exclusion chromatography (SEC) enable purification of the Maleimide/azido-NLPs. Pooled Maleimide/azido-NLP containing fractions are analyzed by native gel electrophoresis, i.e. 4-20% Tris-glycine polyacrylamide gels followed by SyproRuby staining and fluorescent imaging. Typical assemblies are prepared at a 130:1 molar ratio of lipid to E4 22k.

Example 16

Prophetic Example of Covalent Conjugation of an Adjuvant (Thiolated CpG Oligonucleotide) and Antigen (Propargylated Hemagglutinin) to Maleimide/Azido-NLPs Maleimide/azido-NLPs as exemplified in Example 15 can be conjugated with both thiolated CpG oligonucleotide adjuvants and propargylated hemagglutinin antigens.

In particular, commercially available thiolated CpG oligonucleotide adjuvants (e.g. HS-CpG, 22 nucleotides in length with 5' sulfhydryl) are reduced in 5 mM (tris(2-carboxyethyl) phosphine) (TCEP) in TBS buffer (10 mM Tris, 150 mM NaCl). Free TCEP can be removed using a desalting column. The reduced, thiolated oligonucleotide is then incubated with the Maleimide/azido-NLPs at a range of molar ratios between 2 and 50 for 2 hours to produce CpG/azido-NLPs. The reaction product is purified and monitored by SEC. Subsequently, hemagglutinin is propargylated using commercially-available 3-propargyloxypropanoic acid-succinimidyl ester. The alkyne-containing antigen is incubated with the CpG/azido-NLPs in TBS buffer (10 mM Tris, 150 mM NaCl) supplemented with ascorbic acid and copper (II) sulfate for 1 hour to produce CpG/hemagglutinin-NLPs. The reaction product is purified and monitored by SEC and/or native gel electrophoresis.

Example 17

Prophetic Example of NLP Preparation Containing Two Different Functional Anchor Compound Substrate Lipids (Maleimide and Nickel-Chelating) for Covalent Attachment of Adjuvant (Thiolated CpG Oligonucleotide) and Noncovalent Attachment of Antigen (His-Tagged Env)

Maleimide/NiNLPs can be assembled in a similar manner to NiNLPs described in Example 1.

Briefly, lipids (5% 1,2-dihexadecanoyl-sn-glycero-3-phosphoethanolamine-N-[4-(p-maleimidophenyl)butyramide] (sodium salt), 5% DOGS-NTA-Ni and 90% DMPC) are solubilized in chloroform and aliquoted into glass vials and solvent removed in vacuo. Lipids are then dissolved in TBS buffer (10 mM Tris, 150 mM NaCl) using sodium cholate. A typical Maleimide/NiNLP assembly will contain E422K apolipoprotein, lipid, and 20 mM cholate. Samples are incubated at 23.8° C. for at least 1 hour and then dialyzed against TBS. Separation by size exclusion chromatography (SEC) enables purification of the Maleimide/NiNLPs. Pooled Maleimide/NiNLP containing fractions are concentrated using 50 k MWCO spin filters and analyzed by native gel electrophoresis, i.e. 4-20% Tris-glycine polyacrylamide gels followed by SyproRuby staining and fluorescent imaging. Typical assemblies are prepared at a 130:1 molar ratio of lipid to E4 22k.

Example 18

Prophetic Example of Covalent Conjugation of an Adjuvant (Thiolated CpG Oligonucleotide) and Noncovalent Conjugation of a Protein Antigen (His-Tagged Env) to Maleimide/NiNLPs Maleimide/NiNLPs as exemplified in Example 17 can be conjugated to the commercially-available thiolated CpG oligonucleotide adjuvant and His-tagged envelope protein antigen from West Nile virus.

In particular, commercially available thiolated CpG oligonucleotide adjuvant is reduced in 5 mM (tris(2-carboxyethyl)phosphine) (TCEP) in TBS buffer (10 mM Tris, 150 mM NaCl). Free TCEP is then being removed using a desalting column. The reduced, thiolated oligonucleotide is then incubated with the Maleimide/NiNLPs at a molar ratio of 10 for 2 hours. Maleimide/NiNLP:CpG is then purified by SEC. After purification, Maleimide/NiNLP:CpG conjugates are then incubated with His-tagged envelope protein antigen at a molar ratio of 5 for one hour. Conjugation can then be monitored by SEC and/or native gel electrophoresis.

The examples set forth above are provided to give those of ordinary skill in the art a complete disclosure and description of how to make and use the embodiments of the particles, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Petrakova, O., E. Volkova, R. Gorchakov, S. Paessler, R. M. Kinney, and I. Frolov. 2005. Noncytopathic replication of Venezuelan equine encephalitis virus and eastern equine encephalitis virus replicons in Mammalian cells. J Virol 79:7597-608
2. Konishi, E., and P. W. Mason. 1993. Proper maturation of the Japanese encephalitis virus envelope glycoprotein requires cosynthesis with the premembrane protein. J Virol 67:1672-5.
3. Widman, D. G., T. Ishikawa, R. Fayzulin, N. Bourne, and P. W. Mason. 2008. Construction and characterization of a second-generation pseudoinfectious West Nile virus vaccine propagated using a new cultivation system. Vaccine 26:2762-2771
4. Hein, C. D., Liu, X-M, and Wang, D. 2008. Click Chemistry, A Powerful Tool for Pharmaceutical Sciences. Pharmaceutical Research, Vol, 25, No. 10:2216-2230
5. Dalpke, A. H., Zimmermann, S., Albrecht, I. & Heeg, K. 2002. Phosphodiester CpG oligonucleotides as adjuvants: polyguanosine runs enhance cellular uptake and improve immunostimulative activity of phosphodiester CpG oligonucleotides in vitro and in vivo. Immunology 106:102-112
6. Weermata, R. D., McCluskie, M. J., Xu, Y., and Davis, H. L. 2000. CpG DNA induces stronger immune responses with less toxicity than other adjuvants. Vaccine 18:1755-62
7. U.S. Pat. No. 4,317,771 (1982) Muramyl dipeptide derivatives
8. Induction of tumor necrosis factor-a in solid tumor region by the orally administered synthetic muramyl dipeptide analogue, romurtide (2001) Int'l Immunopharm. 1:97-104
9. Polymorphonuclear Leukocyte Activation by a Synthetic Muramyl Dipeptide Analog (1982) Inf. Immun. 38:848-854
10. Huleatta, J. W., Nakaara, V., Desaia, P., Huanga, Y., Hewitta, D., Jacobs, A., Tanga, J., McDonald, W., Song, L., Evans, R. K., Umlauf, S., Tussey, L., and Powell, T. J. 2007. Potent immunogenicity and efficacy of a universal influenza vaccine candidate comprising a recombinant fusion protein linking influenza M2e to the TLR5 ligand flagellin Vaccine 26:201-214
11. Hamdy, S., Haddadi, A., Somayaji, V., Ruan, D. and Samuel, J. 2007. Pharmaceutical analysis of synthetic lipid A-based vaccine adjuvants in poly (d,l-lactic-co-glycolic acid) nanoparticle formulations. Journal of Pharmaceutical and Biomedical Analysis 44:914-923
12. Giannini, S. L., Hanona, E., Moris, P., Van Mechelen, M., Morel, S., Dessy, F., Fourneau, M. A., Colau, B., Suzich, J., Losonksy, G., Martin, M-T., Dubin G., Wettendorff, M. A. 2006. Enhanced humoral and memory B cellular immunity using HPV16/18 L1 VLP vaccine formulated with the MPL/aluminium salt combination ($ASO_4$) compared to aluminium salt only. Vaccine 24:5937-5949
13. Fitzgerald, K. A. and Golenbock, D. T. 2007. The Shape of Things to Come. Science 316:1574-1576

14. Fischer, N. O., Blanchette, C. D., Chromy, B. A., Kuhn, E. A., Segelke, B. W., Corzett, M., Bench, G., Mason, P. W. and Hoeprich, P. D. 2009. "Immobilization of His-tagged Proteins on Nickel-Chelating Nanolipoprotein Particles" Bioconjugate Chemistry 20:460-465

15. Bayburt, T. H.; Grinkova, Y. V.; Sligar, S. G. 2002, "Self-Assembly of Discoidal Phospholipid Bilayer Nanoparticles with Membrane Scaffold Proteins" Nano Lett. 2, 853-856

What is claimed is:

1. An immunostimulatory nanolipoprotein particle comprising:
a scaffold protein,
a functionalized membrane-forming lipid presenting an anchor compound substrate, and at least one of an antigen and/or an adjuvant attaching an anchor compound,
wherein at least one of the at least one of an antigen and/or an adjuvant is attached to the functionalized membrane-forming lipid through binding of the anchor compound substrate with the anchor compound.

2. The immunostimulatory nanolipoprotein particle of claim 1, wherein the anchor compound substrate is a molecule chelating a bivalent metal ion and the anchor compound is a polyhistidine molecule.

3. The immunostimulatory nanolipoprotein particle of claim 2, wherein the bivalent metal ion is selected from the group consisting of $Ni^{2+}$, $Zn^{2+-}$, $Co^{2+}$, and $Cu^{2+}$.

4. The immunostimulatory nanolipoprotein particle of claim 1, wherein the anchor compound substrate is a negatively charged moiety and the anchor compound is a polyarginine molecule.

5. The immunostimulatory nanolipoprotein particle of claim 1, wherein the anchor compound substrate is a glutathione and the anchor compound is Glutathione S-transferase (GST).

6. The immunostimulatory nanolipoprotein particle of claim 1, wherein the anchor compound substrate is biotin and the anchor compound is selected from the group consisting of avidin, streptavidin and neutravidin.

7. The immunostimulatory nanolipoprotein particle of claim 1, wherein the anchor compound substrate is a thiol and the anchor compound is selected from the group consisting of maleimide derivatives, haloacetamides, pyridyldithio-propionate and thiosulfates.

8. The immunostimulatory nanolipoprotein particle of claim 1, wherein the anchor compound substrate is selected from the group consisting of maleimide derivatives, haloacetamides, pyridyldithio-propionate and thiosulfates, and wherein the anchor compound is a thiol-presenting anchor compound.

9. The immunostimulatory nanolipoprotein particle of claim 1, wherein the anchor compound substrate is an amine and the anchor compound is selected from the group consisting of active esters, activated carboxylic acids, isothiocyanates, sulfonyl chlorides, dichlorotriazines, aryl halides and acyl azides.

10. The immunostimulatory nanolipoprotein particle of claim 1, wherein the anchor compound substrate is selected from the group consisting of active esters, activated carboxylic acids, isothiocyanates, sulfonyl chlorides, dichlorotriazines, aryl halides and acyl azides, and wherein the anchor compound is an amine molecule.

11. The immunostimulatory nanolipoprotein particle of claim 1, wherein the anchor compound substrate is an azide molecule and the anchor compound is an acetylene molecule.

12. The immunostimulatory nanolipoprotein particle of claim 1, wherein the anchor compound substrate is an acetylene molecule and the anchor compound is an azide molecule.

13. The immunostimulatory nanolipoprotein particle of claim 1, wherein the anchor compound substrate is selected from the group consisting of hydrazines, hydroxylamines or aromatic amines and the anchor compound is an aldehyde or ketone molecule.

14. The immunostimulatory nanolipoprotein particle of claim 1, wherein the anchor compound substrate is an aldehyde or ketone molecule and the anchor compound is selected from the group consisting of hydrazines, hydroxylamines and aromatic amines.

15. An immunostimulatory nanolipoprotein particle comprising
a functionalized membrane-forming lipid,
a scaffold protein, and
one or more adjuvants
wherein at least one of the one or more adjuvants attaches an anchor compound, and the functionalized membrane-forming lipid attaches a corresponding anchor substrate compound; and
wherein the anchor compound binds the corresponding anchor compound substrate thus attaching each of the one or more adjuvants to the functionalized membrane-forming lipid.

16. The immunostimulatory nanolipoprotein particle of claim 15, wherein the one or more adjuvants attaching an anchor compound are selected from the group consisting of f-Met-Leu-Phe, muramyl dipeptide, saponins, toxis, oligonucloetide CpG motifs, immunostimulatory carbohydrates, immunostimulatory polysaccharides, cytokines, chemokines and derivatives thereof.

17. An immunostimulatory nanolipoprotein particle suitable to attach one or more immunological agents, the immunostimulatory nanoparticle comprising a functionalized membrane-forming lipid,
a scaffold protein, and
at least one adjuvant,
wherein the functionalized membrane-forming lipid presents an anchor compound substrate; and
wherein the anchor compound substrate is capable of binding a corresponding anchor compound presented on the one or more immunological agents.

18. The immunostimulatory nanolipoprotein particle of claim 17, wherein the at least one adjuvant comprises one or more adjuvants selected from the group consisting of hydrophobic adjuvants, amphipathic adjuvants, hydrophilic adjuvants synthetically appended with a hydrophobic moiety.

19. The immunostimulatory nanolipoprotein particle of claim 17, wherein the immunological agent is an antigen selected from the group consisting of viral proteins, bacterial proteins, fungal proteins, proteins from eukaryotic organisms, immunogenic carbohydrate moieties, signaling molecules and derivatives thereof.

20. An immunostimulatory nanolipoprotein particle comprising:
at least one amphipatic adjuvant and a scaffold protein.

21. The immunostimulatory nanolipoprotein particle of claim 20, wherein the at least one amphipatic adjuvant is selected from the group consisting of mono-phosphorylated Lipid A, lipopolysaccharides, squalene, soribitol oleate esters, alpha-galactosyl ceramide, lipotichoic acid and saponins.

22. The immunostimulatory nanolipoprotein particle of claim 20, wherein the at least one amphipatic adjuvants are multiple amphipatic adjuvants.

23. A method to provide an antigen and/or an adjuvant in the immunostimulatory nanolipoprotein particle according to claim 1, the method comprising
attaching the antigen and/or an adjuvant to an anchor compound thus providing an antigen and/or an adjuvant attaching an anchor compound;
attaching the antigen and/or an adjuvant attaching an anchor compound to a nanolipoprotein particle comprising a functionalized membrane-forming lipid, and a scaffold protein,
wherein the functionalized membrane-forming lipid attaches a corresponding anchor compound substrate and the anchor compound binds the corresponding anchor compound substrate, thus attaching the antigen and/or an adjuvant to the functionalized membrane-forming lipid of the nanoparticle.

24. A system for providing an immunological agent in an immunostimulatory nanolipoprotein particle, the system comprising:
an anchor compound, a functionalized membrane-forming lipid, and a scaffold protein,
wherein upon binding of the anchor compound with an immunological agent and upon assembly of the functionalized membrane-forming lipid, the scaffold protein and the immunological agent in a nanolipoprotein particle, the immunological agent is presented on a resulting nanolipoprotein particle.

25. An immunostimulatory composition comprising at least one immunostimulatory nanolipoprotein particle according to claim 1 and a suitable vehicle.

26. A method to stimulate the immune system of an individual, the method comprising administering to the individual at least one of the immunostimulatory nanolipoprotein particles according to claim 1.

27. A system to immunize an individual, the system comprising: the immunostimulatory nanolipoprotein particles of claim 1 and at least one of an antigen and an adjuvant, the immunostimulatory nanolipoprotein particles and the antigen and/or adjuvant to be administered to the individual to immunize the individual.

* * * * *